United States Patent [19]

Semple et al.

[11] Patent Number: 5,728,829
[45] Date of Patent: Mar. 17, 1998

[54] PROCESS OF PREPARING BENZODIAZEPINE COMPOUNDS USEFUL AS ANTAGONISTS OF CCK OR OF GASTRINE

[75] Inventors: Graeme Semple; Hamish Ryder; Michael Szelke, all of Hampshire, United Kingdom; Masato Satoh, Tsukubi, Japan; Mitsuaki Ohta, Tsukuba-gun, Japan; Keiji Miyata, Tsukuba, Japan; Akito Nishida, Niihari-gun, Japan; Masato Ishii, Takahagi, Japan

[73] Assignees: Ferring-Research Limited, Middlesex, United Kingdom; Yamanouchi Pharmaceutical Co. Ltd., Tokyo, Japan

[21] Appl. No.: 591,567

[22] PCT Filed: Aug. 25, 1994

[86] PCT No.: PCT/GB94/01859

§ 371 Date: May 2, 1996

§ 102(e) Date: May 2, 1996

[87] PCT Pub. No.: WO95/06040

PCT Pub. Date: Mar. 2, 1995

[30] Foreign Application Priority Data

Aug. 25, 1993 [GB] United Kingdom ............ 9317693

[51] Int. Cl.$^6$ .............. C07D 243/24; C07D 403/02; A61K 31/33; A61K 31/55
[52] U.S. Cl. .............. 540/509; 540/480; 514/183; 514/212; 514/221
[58] Field of Search .................. 540/480, 509; 514/183, 212, 221

[56] References Cited

U.S. PATENT DOCUMENTS 4,820,834  4/1989  Evans et al. .................. 540/504

FOREIGN PATENT DOCUMENTS

| 0 434 364 | 6/1991 | European Pat. Off. . |
| 0 538 099 | 4/1993 | European Pat. Off. . |
| 0 538 945 | 4/1993 | European Pat. Off. . |
| 2 264 492 | 9/1993 | United Kingdom . |
| 92 11246 | 7/1992 | WIPO . |
| 93 02078 | 4/1993 | WIPO . |
| 93 07131 | 4/1993 | WIPO . |
| 93 16999 | 9/1993 | WIPO . |
| WO 94/00438 | 1/1994 | WIPO . |

OTHER PUBLICATIONS

Fryer et al., "The Chemistry of Heterocyclic Compounds", vol. 50, Chapter VII, (1991) pp. 631–642.
Lotti et al., "A New Potent and Selective Non-Peptide Gastrin Antagonist and Brain Cholecystokinin Receptor (CCK-B) Lingand: L-365,260", E. Jour. Pharmacology, vol. 162, (1989) pp. 273–280.

*Primary Examiner*—Mukund J. Shah
*Assistant Examiner*—Brenda Coleman
*Attorney, Agent, or Firm*—Foley & Lardner

[57] ABSTRACT

A benzodiazepine derivative of formula I, or a pharmaceutically acceptable salt thereof:

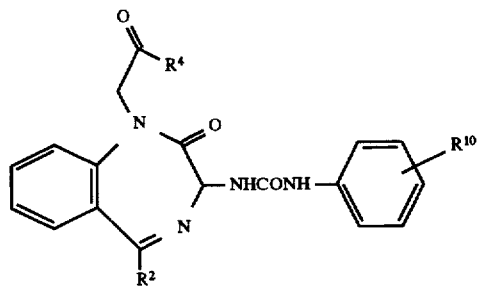

wherein:

(a) $R^4$ is an alkyl, cycloalkyl or aryl group.

(b) $R^{10}$ is chosen from halo, OH, $CH_3$, $OCH_3$, $NR^{11}R^{12}$, $NO_2$, NHCHO, $CO_2H$ and CN, and $R^{11}$ and $R^{12}$ are independently selected from H and alkyl ($C_1$–$C_5$) or together $NR^{11}R^{12}$ form a cyclic structure II,

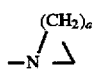

wherein a is 1–6; and (c) $R^2$ is an aromatic 5- or 6-membered, substituted or unsubstituted heterocycle containing at least two heteroatoms of which at least one is nitrogen.

These compounds are gastrin and/or CCK-B receptor antagonists.

6 Claims, No Drawings

5,728,829

1
PROCESS OF PREPARING BENZODIAZEPINE COMPOUNDS USEFUL AS ANTAGONISTS OF CCK OR OF GASTRINE

This application is a 371 of PCT/GB94/01859, filed Aug. 25, 1994, published as WO95/06040 Mar. 2, 1995.

This invention relates to benzodiazepine derivatives which are useful as drugs exhibiting antagonism at the gastrin and/or CCK-B receptor, and to their production.

Many benzodiazepine derivatives have been described in the course of development of psychotropic drugs which act as agonists at the "benzodiazepine receptor" in the central nervous system. More recently benzodiazepine derivatives have been described which act as antagonists at the CCK-A (cholecystokinin-A) and CCK-B receptors. It was further reported that those compounds which were selective antagonists for the CCK-B receptor were able to reduce the secretion of gastric acid in response to the administration of pentagasuin (V J Lotti & R S L Chang, *Eur J Pharmacol* 1989, 162, 273–280). Examples of benzodiazepine derivatives which act as antagonists at the CCK-B receptor are disclosed in, for example, U.S. Pat. No. 4,820,834.

Most of the compounds of the present invention are novel. They differ from the compounds described in U.S. Pat. No. 4,820,834, particularly in the nature of the substituents at positions 1 and 5 of the benzodiazepine nucleus. The present invention includes compounds of superior pharmacological characteristics than those described in U.S. Pat. No. 4,820,834; preferred compounds of the invention have a higher affinity for the CCK-B receptor and/or discriminate more selectively between the CCK-B and CCK-A receptors than the previously described compounds.

The present invention provides a benzodiazepine derivative of formula X, or a pharmaceutically acceptable salt thereof:

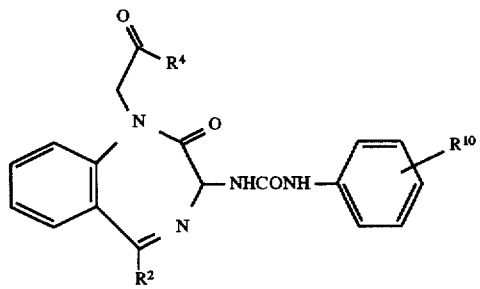

X wherein:
(a) $R^4$ is an alkyl, cycloalkyl or aryl group;
(b) examples of the substituent $R^{10}$ include F, Cl, Br, I, OH, $CH_3$, $OCH_3$, $NO_2$, NHCHO, $CO_2H$, CN and $NR^{11}R^{12}$, where $R^{11}$ and $R^{12}$ are independently selected from H and alkyl ($C_1$–$C_5$) or together with the N they form a cyclic structure XI,

XI and
wherein a is 1–6.
(c) $R^2$ is an aromatic 5- or 6-membered substituted or unsubstituted heterocycle containing at least two heteroatoms of which at least one is nitrogen.

Herein all 'alkyl' and 'cycloalkyl' groups are preferably of up to 8 carbon atoms. When $R^4$ is an aromatic residue it may be mono or disubstituted, and it is preferably monocyclic.

2

Preferably the substituent $R^{10}$ is at the meta position of the phenyl ring.

Preferably $R^2$ is an unsubstituted or monosubstituted heterocycle containing two heteroatoms of which at least one is nitrogen.

Most preferably $R^4$ is tert-butyl or 2-, 3- or 4-methylphenyl.

Most preferably $R^2$ is selected from 2-pyrimidine, 4-pyrimidine, 2-pyrazine, 6-pyridazine, 2-thiazole, 4-thiazole, 2-oxazole, 4-oxazole, 3-pyrazole, 5-pyrazole, 3-isoxazole, 3-isothiazole, 2-imidazole, 4-imidazole, 5-imictazole, 2-(N-methyl)imidazole, 4-(N-methyl)imidazole and 5-(N-methyl)imidazole.

The compounds of this invention all have at least one stereogenic centre and so can exist as optical isomers. It should be understood that these isomers, either separately or as mixtures, are included within the scope of this invention. In preferred compounds according to the invention, the absolute configuration at the 3-position of the benzodiazepine ring is R (as shown in XII).

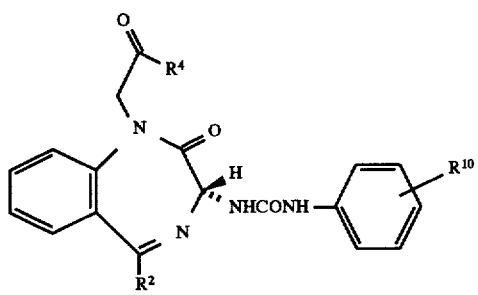

XII

Amongst preferred compounds according to the invention are those listed below and salts thereof. Some of the compounds are exemplified hereinafter as indicated against the individual compounds concerned.

LIST A

1. N-((3RS)- 1-tert-Butylcarbonylmethyl-2,3-dihydro-2-oxo-5-(2-thiazolyl)- 1H- 1,4-benzodiazepin-3-yl)-N'-(3-methylphenyl) area (Example 3);
2. N-((3RS)- 1-tert-Butylcarbonylmethyl-2,3-dihydro-2-oxo-5-(2-thiazolyl)- 1H- 1,4-benzodiazepin-3-yl)-N'-(3-dimethylaminophenyl)urea(Example 4);
3. N-((3RS)- 1-tert-B utylcarbonylmethyl-2,3-dihydro-5-(2-(1-methyl)imldazolyl)-2-oxo-1H-1,4-benzodiazepin-3-yl)-N'-(3-methylphenyl)urea(Example 1 );
4. N-((3RS)- 1-tert-Butylcarbonylmethyl-2,3-dihydro-5-(2-(1-methyl)imidazolyl)-2-oxo-1H-1,4-benzodiazepin-3-yl)-N'-(3-dimethytaminophenyl)urea(Example 2);
5. N-((3RS)- 1-tert-Butylcarbonylmethyl-2,3-dihydro-5-(2-imidazolyl)-2-oxo-1H-1,4-benzodiazepin-3-yl)-N'-(3-methylphenyl)urea(Example 7);
6. N-((3RS)-1-tert-Butylcarbonylmethyl-2,3-dihydro-5-(2-imidazolyl)-2-oxo-1H-1,4-benzodiazepin-3-yl)-N'-(3-dimethylaminophenyl)urea(Example 8);
7. N-((3RS)-1-tert-Butylcarbonylmethyl-2,3-dihydro-5-(4-imidazolyl)-2-oxo-1H-1,4-benzodiazepin-3-yl)-N'-(3-methylphenyl)urea(Example 10);
8. N-((3 RS)-1-tert-Butylcarbonylmethyl-2,3-dihydro-5-(4-imidazolyl)-2-oxo-1H-1,4-benzodiazepin-3-yl)-N'-(3-dimethylaminophenyl)urea(Example 11);
9. N-((3RS)-1-tert-Butylcarbonylmethyl-2,3-dihydro-2-oxo-5-(3-pyrazolyl)-1H-1,4-benzodiazepin-3-yl)-N'-(3-methylphenyl)urea(Example 13);
10. N-((3RS)-1-tert-Butylcarbonytmethyl-2,3-dihydro-2-oxo-5-(3-pymzolyl)- 1H-1,4-benzodiazepin-3-yl)-N'-(3-dimethylamirtophenyl)urea;

11. N-((3RS)-1-tert-Butylcarbonylmethyl-2,3-dihydro-2-oxo-5-(3-pyridazinyl)-1H-1,4-benzodiazepin-3-yl)-N'-(3-methylphenyl)urea;
12. N-((3RS)-1-tert-Butylcarbonyimethyl-2,3-dihydro-2-oxo-5-(3-pyridazinyl)-1H-1,4-benzodiazepin-3-yl)-N'-(3-dimethylaminophenyl)urea;
13. N-((3RS)-1-tert-Butylcarbonylmethyl-2,3-dihydro-2-oxo-5-(2-pyrimidinyl)-1H-1,4-benzodiazepin-3-yl)-N'-(3-methylphenyl)urea;
14. N-((3RS)-1-tert-Butylcarbonylmethyl-2,3-dihydro-2-oxo-5-(2-pyrimidinyl)-1H-1,4-benzodiazepin-3-yl)-N'-(3-dimethylaminophenyl)urea;
15. N-((3RS)-1-tert-Butylcarbonylmethyl-2,3-dihydro-2-oxo-5-(4-pyrimidinyl)-1H-1,4-benzodiazepin-3-yl)-N'-(3-methylphenyl)urea;
16. N-((3RS)-1-tert-Butylcarbonyimethyl-2,3-dihydro-2-oxo-5-(4-pyrimidinyl)-1H-1,4-benzodiazepin-3-yl)-N'-(3-dimethylaminophenyl)urea;
17. N-((3RS)-1-tert-Butylcarbonylmethyl-2,3-dihydro-2-oxo-5-(2-pyrazinyl)-1H-1,4-benzodiazepin-3-yl)-N'-(3-methylphenyl)urea(Example 5);
18. N-((3RS)-1-tert-Butylcarbonylmethyl-2,3-dihydro-2-oxo-5-(2-pyrazinyl)-1H-1,4-benzodiazepin-3-yl)-N'-(3-dimethylaminophenyl)urea(Example 6);
19. N-((3RS)-1-tert-Butylcarbonylmethyl-2,3-dihydro-5-(2-imidazolyl)-2-oxo-1H-1,4-benzodiazepin-3-yl)-N'-(3-(1-pyrollidinyl)phenyl)urea(Example 9);
20. N-((3RS)-2,3-Dihydro-5-(4-imidazolyl)-1-(4-methylphenylcarbonylmethyl)-2-oxo-1H-1,4-benzodiazepin-3-yl)-N'-(3-methylphenyl)urea(Example 12).

The compounds of the invention can be prepared according to the general route outlined below (Scheme 1).

Where $R^2$ contains NH as part of the heterocycle a suitable protecting group may be required for pan or all of the synthetic route outlined in Scheme 1, and a final deprotection step may be required. The aminobenzoyl starting material, if previously reported, was prepared using literature routes. Previously unreponed starting materials were prepared using standard methodology, the details of which are described below.

Among the reports of benzodiazepine derivatives acting as CCK-A, CCK-B or gastrin receptor antagonists the most frequently encountered substitution pattern is the 3-acylamino-5-aryl-2,3-dihydro-1H,-1,4-benzodiazepin-2-one with a variety of substituents at N-1. Previously described syntheses of 3-amino-5-aryl substituted 2,3-dihydro-1H-1,4-benzodiazepin-2-ones either introduce the 3-amino function by nitrosation and reduction of a 3-unsubstituted benzodiazepine or start with an α-alkylthioglycine derivative and cyclise this to give directly a protected 3-aminobenzodiazepine. The nitrosation/reduction route fails when the 5-aryl substituent is other than (substituted) phenyl while the alkylthioglycine route involves the use of unpleasant alkylmercaptans and requires the mediation of highly toxic mercuric salts. The process of this invention avoids the use of environmentally unacceptable reagents and is generally applicable to any 5-aryl substituent.

Scheme 1

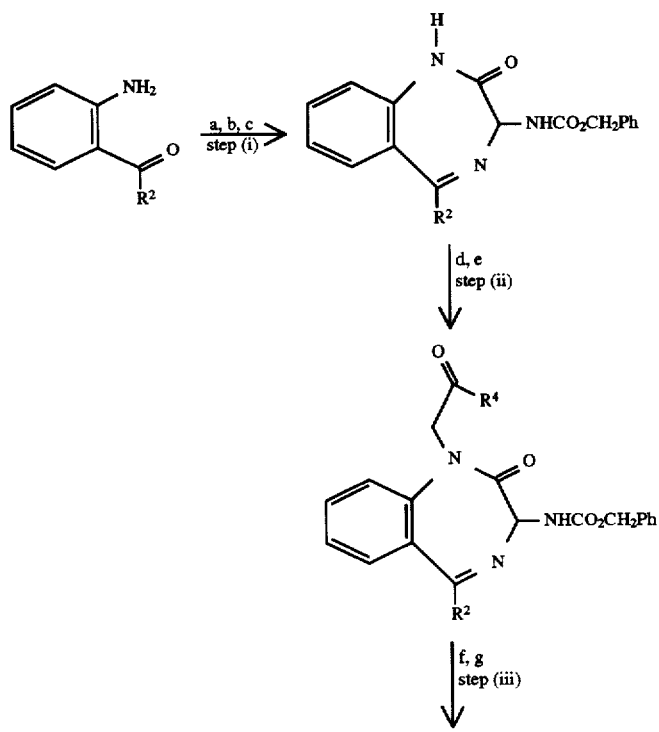

-continued
Scheme 1

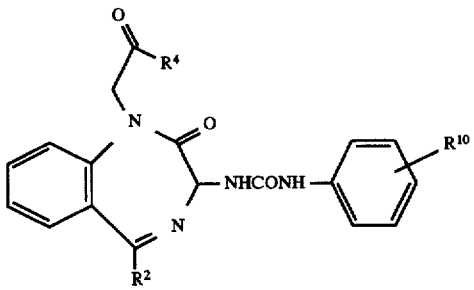

Reagents: (a) PhCH₂OCONH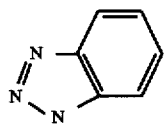CO₂H, WSCI, DMAP; (b) NH₃, MeOH;

(c) NH₄OAc, AcOH; (d) NaH, DMF; (e) R⁴COCH₂Br;

(f) HBr, DCM or H₂, Pd/C; (g) 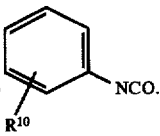NCO.

The present invention provides a process for the production of benzodiazepines of general formula V or pharmaceutically active salts thereof which comprises the coupling reaction of an-optionally substituted N-protected α-(1-benzotriazolyl)glycine derivative (II) with an aromatic or heterocyclic amino ketone (III), followed by reaction of the intermediate (IV) with ammonia and then an acid catalysed cyclisation of the resultant amino-ketone

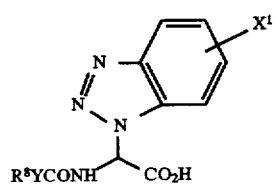

II

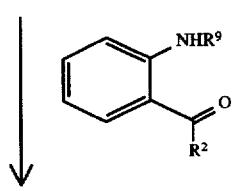

III

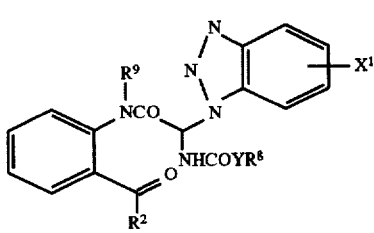

IV (i) NH₃
(ii) H⁺

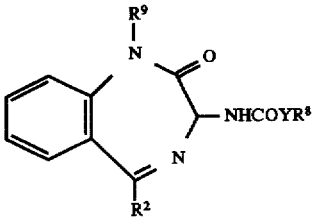

V wherein:
R² is an optionally substituted aromatic carbocyclic or heterocyclic group;
R⁸ is a lower alkyl (C₁-C₆, linear or branched), a cycloalkyl (C₃-C₈), or an optionally substituted aralkyl, aryl or heteroaryl group;
R⁹ is H, lower alkyl (C₁-C₆, linear or branched) or CH₂COR⁴ where R⁴ is an alkyl (preferably C₁-C₆, linear or branched), a cycloalkyl (preferably C₃-C₈), or an optionally substituted aryl, heteroaryl or saturated heterocyclic group;
X¹ is H, alkyl (C₁-C₃), alkyloxy (C₁-C₃), F, Cl or Br; and
Y is —O—, —NH— or a single bond.
Preferably, R⁸ is a lower alkyl (C₁-C₆, linear or branched), a cycloalkyl (C₃-C₈), or an optionally substituted benzyl, phenyl or heteroaryl group;
R⁹ is H or lower alkyl (C₁-C₆, linear or branched);
X¹ is H; and
Y is —O—.

The process of the invention can of course produce compounds of formula X above, including the specified preferred embodiments thereof.

Herein aryl means aromatic cyclic and includes both carbocyclic and heterocyclic aromatics.

Benzodiazepines obtainable by the process of the invention, or readily prepared from products of said process, include those of formula I and salts thereof:

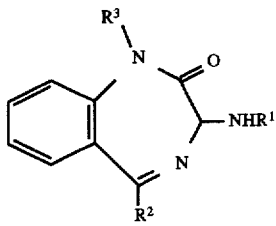

wherein:

(a) —NHR$^1$ is an alkyl (C$_1$–C$_6$, linear or branched), cycloalkyl (C$_3$–C$_8$), or optionally substituted aralkyl, aryl or heteroaryl carbamate group or R$^1$ is H or —CONHR$^5$ where R$^5$ is an alkyl (C$_1$–C$_6$, linear or branched), a cycloalkyl (C$_3$–C$_8$), or an optionally substituted aromatic carbocyclic or heterocyclic or aralkyl group;

(b) R$^2$ is an optionally substituted aromatic carbocyclic or heterocyclic group; and (c) R$^3$ is H, alkyl (C$_1$–C$_6$, linear or branched), or —CH$_2$COR$^4$ where R$^4$ is a lower alkyl (C$_1$–C$_6$, linear or branched), cycloalkyl (C$_3$–C$_8$) or an optionally substituted aryl (e.g. phenyl), heteroaryl or saturated heterocyclic group.

Preferably R$^1$ is H or tert-butyloxycarbonyl, methyloxycarbonyl, ethyloxycarbonyl or benzyloxycarbonyl or —CONHR$^5$.

Preferably R$^2$ is pyridyl, pyridazinyl, pyrimidinyl, pyrazinyl, thiazolyl, isothiazolyl, methyl-imidazolyl, oxazolyl, isoxazolyl, optionally protected pyrazolyl or imidazolyl or optionally substituted phenyl.

Preferably R$^3$ is H or CH$_2$COR$^4$.

Preferably R$^4$ is tert-butyl, cycloalkyl C$_3$–C$_7$ or 2-, 3- or 4-methyl phenyl.

Preferably R$^5$ is a phenyl group substituted at the 3-position with a substituent selected from F, Cl, Br, OH, OCH$_3$, NO$_2$, CH$_3$, CO$_2$H, SO$_3$H, tetrazolyl and NR$^6$R$^7$ where R$^6$ and R$^7$ are independently H, C$_1$–C$_3$ alkyl, a recognised nitrogen protecting group or together form a 3–7 reinserted ring with nitrogen.

Most preferably R$^2$ is 2-, 3- or 4-substituted pyridyl or phenyl.

Most preferably R$^5$ is a phenyl group substituted in the 3-position with a substituent selected from CH$_3$ and NR$^6$R$^7$, where R$^6$ and R$^7$ are preferably independently selected from H, CH$_3$, ethyl, formyl, tert-butyloxycarbonyl, and benzyloxycarbonyl or together are an alkylidene chain which forms a 3–6 membered ring with the nitrogen.

The compounds of formulae V and I and theft salts all have at least one stereogenic centre and so can exist as optical isomers. It should be understood that the preparation of these isomers, either separately or as mixtures, is included within the scope of this invention. Compounds of formulae X, V and I can form salts with inorganic or organic acids or, in some cases, bases. Examples of such salts would include chlorides, sulphates and acetates, or sodium and potassium salts. Salts and their preparation should also be understood to be included within the scope of this invention.

Compounds of formulae X, V and I and their salts include compounds which can act as CCK-B and/or gastrin receptor antagonists and which may be used as drugs for the treatment of diseases induced by the failure of a physiological function controlled by gastrin, such as gastric and duodenal ulcers, gastrins, reflux esophagatis, gastric and colon cancers, and Zollinger-Ellison syndrome; there may be no side effects arising from CCK-A receptor interaction. The drugs may be used for the treatment of diseases induced by the failure of physiological function controlled by the central CCK-B receptor (e.g. for the reduction of anxiety or for appetite regulation).

Amongst preferred compounds of formula V or I are those listed below and salts thereof. The compounds are exemplified hereinafter to demonstrate the scope and utility of the process herein described, as indicated against the individual compounds.

LIST B 1 (3RS)-(Ethoxycarbonyl)amino-2,3-dihydro-5-(2-pyridyl)-1-H-4-benzodiazepin-2-one (Example 16)

2 (3RS)-(Ethoxycarbonyl)amino-1-(tert-butylcarbonylmethyl)-2,3-dihydro-5-(2-pyridyl)-1H-1,4-benzodiazepin-2-one (Example 17)

3 (3RS)-Amino-1-(tert-butylcarbonylmethyl)-2,3-dihydro-5-(2-pyridyl)-(1H)-1,4-benzodiazepin-2-one (Example 18)

4 (3R)-Amino-1-(tert-butylcarbonylmethyl)-2,3-dihydro-5-(2-pyridyl)-(1H)-1,4-benzodiazepin-2-one (Example 19)

5 (3S)-Amino-1-(tert-butylcarbonylmethyl)-2,3-dihydro-5-(2-pyridyl)-(1H)-1,4-benzodiazepin-2-one (Example 20)

6 N-((3R)-1-tert-Butylcarbonylmethyl-2,3-dihydro-2-oxo-5-(2-pyridyl)-1H-1,4-benzodiazepin-3-yl)-N'-((3-dimethylamino)phenyl)urea (Example 22)

7 N-((3RS)-1-tert-Butylcarbonylmethyl-2,3-dihydro-2-oxo-5-(2-pyridyl)-1H-1,4-benzodiazepin-3-yl)-N'-(3-(N-formyl-N-methylamino)phenyl)urea (Example 25)

8 N-((3RS)-1-tert-Butylcarbonylmethyl-2,3-dihydro-2-oxo-5-(2-pyridyl)-1H-1,4-benzodiazepin-3-yl)-N'-((3-methylamino)phenyl)urea (Example 26)

9 N-((3R)-1-tert-Butylcarbonylmethyl-2,3-dihydro-2-oxo-5-(2-pyridyl)-1H-1,4-benzodiazepin-3-yl)-N'-(3-aminophenyl)urea (Example 28)

10 (3RS)-Benzyloxycarbonylamino-2,3-dihydro-5-(2-(1-methyl)imidazolyl)-1H-1,4-benzodiazepin-2-one (Example 1C)

11 (3RS)-Benzyloxycarbonylamino-1-tert-butylcarbonylmethyl-2,3-dihydro-5-(2-(1-methyl)imidazolyl)-1H-1,4-benzodiazepin-2-one (Example 1D)

12 (3RS)-3-Amino-1-tert-butylcarbonylmethyl-2,3-dihydro-5-(2-(1-methyl)imidazolyl)-1H-1,4-benzodiazepin-2-one (Example 1E)

13 N-((3RS)-1-tert-Butylcarbonylmethyl-2,3-dihydro-2-oxo-5-(2-(1-methyl)imidazolyl)-1H-1,4-benzodiazepin-3-yl)-N'-(3-methylphenyl)urea (Example 1F)

14 N-((3RS)-1-tert-Butylcarbonylmethyl-2,3-dihydro-2-oxo-5-(2-(1-methyl)imidazolyl)-1H-1,4-benzodiazepin-3-yl)-N'-(3-dimethylaminophenyl)urea (Example 2)

15 (3RS)-Benzyloxycarbonylamino-2,3-dihydro-5-(2-thiazolyl)-1H-1,4-benzodiazepin-2-one (Example 3B)

16 (3RS)-Benzyloxycarbonylamino-1-tert-butylcarbonylmethyl-2,3-dihydro-5-(2-thiazolyl)-1H-1,4-benzodiazepin-2-one (Example 3C)

17 (3RS)-Amino-1-tert-butylcarbonytmethyl-2,3-dihydro-5-(2-thiazolyl)-1H-1,4-benzodiazepin-2-one (Example 3D)

18 N-((3RS)-1-tert-Butylcarbonylmethyl-2,3-dihydro-2-oxo-5-(2-thiazolyl)-1H-1,4-benzodiazepin-3-yl)-N'-(3-methylphenyl)urea (Example 3E)

19 N-((3RS)-1-tert-Butylcarbonylmethyl-2,3-dihydro-2-oxo-5-(2-thiazolyl)-1H-1,4-benzodiazepin-3-yl)-N'-(3-dimethylaminophenyl)urea (Example 4)

20 (3RS)-Benzyloxycarbonylamino-2,3-dihydro-5-(2-pyrazinyl)-1H-1,4-benzodiazepin-2-one (Example 5D)

21 (3RS)-Benzyloxycarbonylamino-1-tert-butylcarbonylmethyl-2,3-dihydro-5-(2-pyrazinyl)-1H-1,4-benzodiazepin-2-one (Example 5E)

22 (3RS)-Amino-1-tert-butylcarbonytmethyl-2,3-dihydro-5-(2-pyrazinyl)-1H-1,4-benzodiazepin-2-one (Example 5F)

23 N-((3RS)-1-tert-Butylcarbonylmethyl-2,3-dihydro-2-oxo-5-(2-pyrazinyl)-1H-1,4-benzodiazepin-3-yl)-N'-(3-methylphenyl)urea (Example 5G)

24 N-((3RS)-1-tert-Butylcarbonylmethyl-2,3-dihydro-2-oxo-5-(2-pyrazinyl)-1H-1,4-benzodiazepin-3-yl)-N'-(3-dimethylaminophenyl)urea (Example 6)

25 (3RS)-Benzyloxycarbonylamino-2,3-dihydro-5-(1-((2-trimethylsilyl)ethoxy)methyl)imidazol-2-yl)-1H-1,4-benzodiazepin-2-one (Example 7E)

26 (3RS)-Benzyloxycarbonylamino-1-tert-butylcarbonylmethyl-2,3-dihydro-5-(1-((2-trimethylsilyl)ethoxy)methyl)imidazol-2-yl)-1H-1,4-benzodiazepin-2-one (Example 7F)

27 N-((3RS)-1-tert-Butylcarbonylmethyl-2,3-dihydro-2-oxo-5-(1-((2-trimethylsilyl)ethoxy)methyl)imidazol-2-yl)-1H-1,4-benzodiazepin-3-yl)-N'-(3-methylphenyl)urea (Example 7G)

28 N-((3RS)-1-tert-Butylcarbonylmethyl-2,3-dihydro-2-oxo-5-(2-imidazolyl)-1H-1,4-benzodiazepin-3-yl)-N'-(3-methylphenyl)urea (Example 7H)

29 N-((3RS)-1-tert-Butylcarbonylmethyl-2,3-dihydro-2-oxo-5-(1-((2-trimethylsilyl)ethoxy)methyl)imidazol-2-yl)-1H-1,4-benzodiazepin-3-yl)-N'-(3-dimethyl aminophenyl)urea (Example 8A)

30 N-((3RS)-1-tert-Butylcarbonylmethyl-2,3-dihydro-5-(2-imidazolyl)-2-oxo-1H-1,4-benzodiazepin-3-yl)-N'-(3-dimethylaminophenyl)urea (Example 8B)

31 N-((3RS)-1-tert-Butylcarbonylmethyl-2,3-dihydro-2-oxo-5-(1-((2-trimethylsilyl)ethoxy)methyl)imidazol-2-yl)-1H-1,4-benzodiazepin-3-yl)-N'-(3-(1-pyrrolidyl)phenyl)urea (Example 9B)

32 N-((3RS)-1-tert-Butylcarbonylmethyl-2,3-dihydro-5-(2-imidazolyl)-2-oxo-1H-1,4-benzodiazepin-3-yl)-N'-(3-(1-pyrrolidyl)phenyl)urea (Example 9C)

33 (3RS)-Benzyloxycarbonylamino-2,3-dihydro-5-(1-((2-trimethylsilyl)ethoxy)methyl)imidazol-4-yl)-1H-1,4-benzodiazepin-2-one (Example 10F)

34 (3RS)-Benzyloxycarbonylamino-1-tert-butylcarbonylmethyl-2,3-dihydro-5-(1-((2-trimethylsilyl)ethoxy)methyl)imidazol-4-yl)-1H-1,4-benzodiazepin-2-one (Example 10G)

35 N-((3RS)-1-tert-Butylcarbonylmethyl-2,3-dihydro-2-oxo-5-(1-((2-trimethylsilyl)ethoxy)methyl)imidazol-4-yl)-1H-1,4-benzodiazepin-3-yl)-N'-(3-methylphenyl)urea (Example 10H)

36 N-((3RS)-1-tert-Butylcarbonylmethyl-2,3-dihydro-2-oxo-5-(4-imidazolyl)-1H-1,4-benzodiazepin-3-yl)-N'-(3-methylphenyl)urea (Example 10I)

37 N-((3RS)-1-tert-Butylcarbonylmethyl-2,3-dihydro-2-oxo-5-(1-((2-trimethylsilyl)ethoxy)methyl)-imidazol-4-yl)-1H-1,4-benzodiazepin-3-yl)-N'-(3-dimethylaminophenyl)urea 38 N-((3RS)-1-tert-Butylcarbonylmethyl-2,3-dihydro-2-oxo-5-(4-imidazolyl)-1H-1,4-benzodiazepin-3-yl)-N'-(3-dimethylaminophenyl)urea (Example 11B)

39 (3RS)-Benzyloxycarbonylamino-2,3-dihydro-5-(1-((2-trimethylsilyl)ethoxy)methyl)pyrazol-3-yl)-1H-1,4-benzodiazepin-2-one (Example 13G)

40 (3RS)-Benzyloxycarbonylamino-2,3-dihydro-5-(1-((2-trimethytsilyl)ethoxy)methyl)pyrazol-5-yl)-1H-1,4-benzodiazepin-2-one (Example 13H)

41 (3RS)-Benzyloxycarbonylamino-1-tert-butylcarbonylmethyl-2,3-dihydro-5-(1-((2-(trimethylsilyl)ethoxy)methyl)pyrazol-3-yl)-1H-1,4-benzodiazepin-2-one (Example 13I)

42 (3RS)-Benzyloxycarbonylamino-1-tert-butylcarbonylmethyl-2,3-dihydro-5-(1-((2-(trimethylsilyl)ethoxy)methyl)pyrazol-5-yl)-1H-1,4-benzodiazepin-2-one (Example 13J)

43 (3RS)-Amino-1-tert-butylcarbonylmethyl-2,3-dihydro-5-(3-pyrazolyl)-1H-1,4-benzodiazepin-2-one (Example 13K)

44 N-((3 RS)-1-tert-Butylcarbonylmethyl-2,3-dihydro-2-oxo-5-(3-pyrazolyl)-1H-1,4-benzodiazepin-3-yl-N'-(3-methylphenyl)urea (Example 13L)

45 (3RS)-Benzyloxycarbonylamino-2,3-dihydro-2-oxo-5-(3-pyridazinyl)-1H-1,4-benzodiazepin-2-one (Example 32)

46 (3RS)-Benzyloxycarbonylamino-1tert-Butylcarbonylmethyl-2,3-dihydro-5-(3-pyridazinyl)-1H-1,4-benzodiazepin-2-one (Example 33)

47 N-((3RS)-1-tert-Butylcarbonylmethyl-2,3-dihydro-2-oxo-5-(3-pyridazinyl)-1H-1,4-benzodiazepin-3-yl)-N'-(3-dimethylaminophenyl)urea (Example 34)

48 N-(3R)-1-tert-Butylcarbonylmethyl-2,3-dihydro-2-oxo-5-(2-pyridyl)-1H-1,4-benzodiazepin-3-yl-N'-(3-(1-piperidinyl)phenyl)urea (Example 40)

49 (3RS)-tert-Butyloxycarbonylamino-2,3-dihydro-2-oxo-5-phenyl-1H-1,4-benzodiazepin-2-one (Example 41)

50 ((3R)-1-tert-Butylcarbonylmethyl-2,3-dihydro-2-oxo-5-(2-pyridyl)-1H-1,4-benzodiazepin-3-yl)-N'-(3-methylphenyl)urea (Example 42)

51 N-((3R)-1-tert-Butylcarbonytmethyl-2,3-dihydro-2-oxo-5-(2-pyridyl)-1H-1,4-benzodiazepin-3-yl)-N'-(3-methylaminophenyl)urea (Example 52) and the N-((3R)-isomers of compounds 7 and 8 above.

Preferred processes of this invention are outlined in Scheme 2:

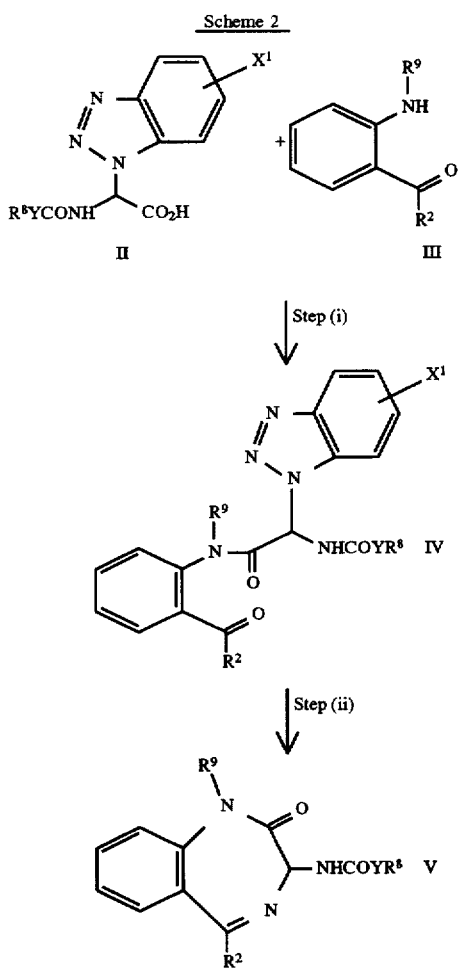

where $R^2$ is as defined above; $R^8$ is alkyl $(C_1-C_6)$, cycloalkyl $(C_3-C_8)$, optionally substituted benzyl or optionally substituted aryl; $R^9$ is H or alkyl $(C_1-C_6)$; $X^1$ is H, alkyl $(C_1-C_3)$, alkyloxy $(C_1-C_3)$ or halide; and Y is —O—, —NH— or a single bond. Preferably $R^8$ is methyl, ethyl, tert-butyl or benzyl; $R^9$ is H or methyl; $X^1$ is H; and Y is —O—.

In step (i) a protected α-benzotriazolylglycine derivative II is condensed with an amine III. This may be achieved using any of the methods known to effect amide bond formation. The acid is either converted into a reactive derivative (for example the acid chloride by treatment with e.g. thionylchloride or oxalyl chloride, a mixed anhydride by reaction with e.g.-ethyl chloroformate or isobutyl chloroformate, or the symmetrical anhydride by treatment with e.g. acetic anhydride or dicyclohexylcarbodiimide) or it is premixed with the amine III and the mixture is treated with a condensing agent. Such an agent may be chosen from, but is not limited to, a carbodiimide (for example dicyclohexyl carbodiimide, N-ethyl-N'-dimethylaminopropyl carbodiimide), BOP-CI (bis(2-oxo-3-oxazolidinyl) phosphoryl chloride), EEDQ (2-ethoxy-1-ethoxycarbonyl-1,2-dihydroquinoline), PyBroP (bromo-tris-pyrrolidino- phosphonium hexafluorophosphate), and HBTU (O-benzotriazolyl-tetramethylisouronium hexafluorophosphate). With some of these reagents it is beneficial to add a catalyst. These catalysts are generally known, and include for example, DMAP (4-dimethylaminopyridine), hydroxybenzotriazole, and pentafluorophenol. It will also, on occasion, be found necessary to add a base to the reaction. In these cases the base is usually an organic amine, for example triethylamine or N-methylmorpholine. The solvent for the reaction is any organic solvent or mixture of solvents which does not react with any of the reagents used. Suitable solvents include but are not limited to dichloromethane, chloroform, ethyl acetate, dimethylformamide, tetrahydrofuran and toluene. Preferably the reaction is performed by treating a mixture of II and III with a carbodiimide, most preferably dicyclohexylcaxbodiimide or N-ethyl-N'-dimethylaminopropyl carbodiimide, in the presence of DMAP as catalyst and with dichloromethane as solvent. Depending on the exact nature of the reagents used and the substituents present the temperature at which the reaction is carried out can be between −80° C. and the boiling point of the solvent used. Preferably it is between −20° C. and the boiling point of the solvent, and most preferably it is between −5° C. and 25° C.

The amide IV can be purified, for example by crystallisation or chromatography, but in general this is not necessary, in which case it is preferable to use the crude product IV in step (ii) directly.

In step (ii) the benzotriazolylamide IV is first reacted with ammonia, either in liquid ammonia without a solvent or using a solution of ammonia in a solvent. The solvent is either water or preferably an organic solvent such as an alcohol, THF, diethyl ether, or dioxan. More preferably it is an alcohol, and most preferably methanol or ethanol or a mixture based on methanol or ethanol (such as industrial methylated spirit).

In the second part of step (ii) the product of this reaction with ammonia is cyclised to give the benzodiazepine V. Preferably this is performed by treatment with acid. More preferably this acid is an organic carboxylic acid, and most preferably acetic acid. It may also be advantageous to add ammonium acetate. When the acid is a liquid it is not always necessary to use a solvent for this reaction. When the acid is a solid, or is a liquid in which the other reaction component does not dissolve, then a solvent can be used. This solvent is any organic solvent. In the preferred case where the acid is acetic acid then no solvent is necessary and it is preferred that none be added.

Each part of step (ii) may be carried out at any temperature between −80° C. and the boiling point of the solvent, and preferably between −20° C. and the boiling point of the solvent. Most preferably the first part is performed between −5° C. and 30° C., and the second part is performed between 10° C. and 30° C.

Often benzodiazepine V will not be the final active CCK or gastrin receptor antagonist, but a useful intermediate for the synthesis of such a compound. A preferred such transformation is illustrated in Schemes 3 and 4.

Scheme 3

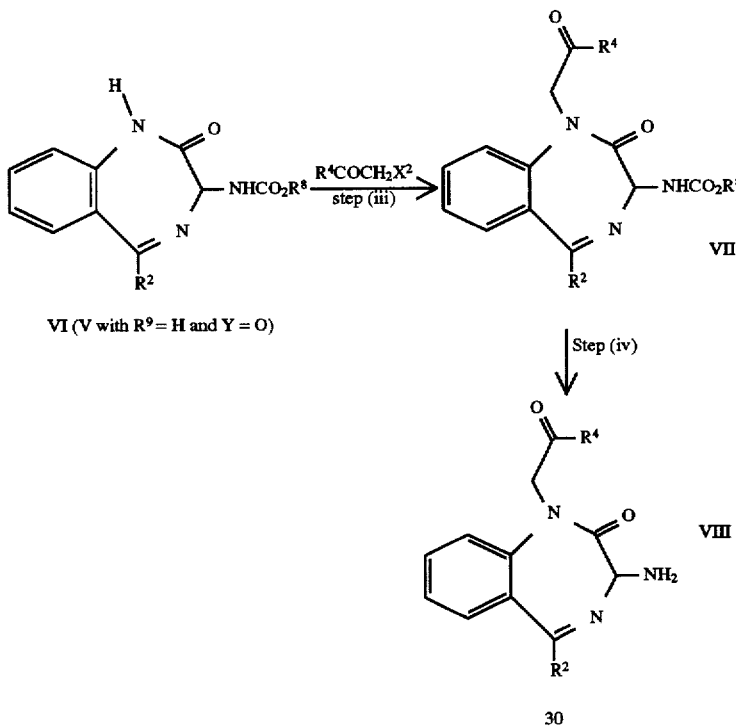

VI (V with $R^9$ = H and Y = O)

where $R^4$ is described above; and $X^2$ is chosen from a halogen atom (chloride, bromide, iodide) or an organic sulphonate (for example methanesulphonate, tosylate, trifluoromethanesulphonate). Preferably $X^2$ is a halogen and most preferably bromide.

In step (iii) the benzodiazepine VI is alkylated. This requires the use of a base to deprotonate the nitrogen atom which is involved in the reaction. The base can either be added to VI to preform the deprotonated species before addition of the alkylating agent or it can be added to a mixture of VI and the alkylating agent. The base used can be any strong base, and is preferably a metal hydride (e.g. sodium or potassium hydride), a metal alkoxide (e.g. sodium methoxide, potassium t-butoxide, a metal amide (e.g. sodium amide, $NaNH_2$), or a metal hydroxide (e.g. sodium hydroxide). Most preferably it is sodium hydride. The solvent for the reaction is any solvent compatible with the base used. Preferably it is a dipolar aprotic solvent and most preferably it is dimethylformamide. An alternative preferred solvent is a mixture of water and an organic solvent such as toluene. This mixture of solvents requires the inclusion of a phase-transfer catalyst (which can be chosen from any known phase-transfer catalyst) and is best suited to the use of metal hydroxides as base. The reaction is performed at any temperature between $-80°$ C. and the boiling point of the solvent and preferably between $-10°$ C. and $30°$ C.

In step (iv) the carbamate protecting group is removed. The conditions appropriate will depend on the nature of $R^8$ and are generally well known. Examples of such conditions are the use of strong acids (e.g. HCl, HBr, $CF_3CO_2H$), strong bases (e.g. NaOH), and hydrogenolysis over a catalyst (e.g. Pt-on-C, Pd-on-C). One preferred set of conditions which is applicable for most of the preferred examples of $R^8$ is the use of HBr in dichloromethane.

Scheme 4

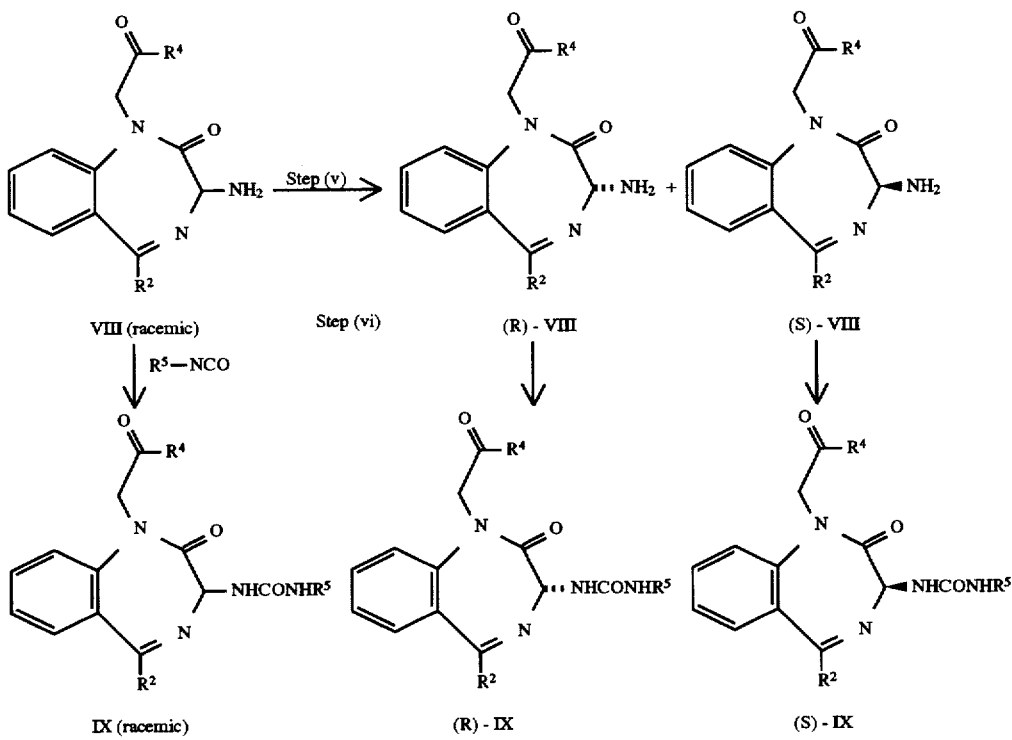

where R⁵ is as described above.

Racemic amine VII can be resolved into two enantiomers by any method known for the resolution of amines. Preferably it is resolved by crystallisation in the presence of a single enantiomer of a chiral acid. This acid may be chosen from any of the known chiral acids, for example tartaric acid, lactic acid, and camphorsulphonic acid. Preferably the acid is mandelic acid. Most preferably it is (R)-mandelic acid, in which case when $R^2$ is 2-pyridyl, the salt with the (R)-aminobenzodiazepine crystallises.

The amine VIII, and preferably a single enantiomer of VIII, can be reacted with an isocyanate R⁵NCO to give a urea IX. This reaction is best performed in a solvent. The solvent is preferably a common organic solvent which does not react with the reaction components. Examples of such solvents are toluene, THF, dichloromethane and ethyl acetate. Most preferably the solvent is a chlorinated hydrocarbon such as dichloromethane.

The reaction can be performed at any temperature between –80° C. and the boiling point of the solvent. Preferably it is performed between –20° C. and the boiling point of the solvent, and most preferably between –10° C. and 30° C.

When the heterocyclic amino ketone, III, contains a reactive nitrogen atom, this atom may be protected by a suitable aromatic nitrogen protecting group (such as trimethylsilylethoxymethyl) during the synthetic steps (i) to (vi). This group can be unmasked at a late stage or preferably after steps (i) to (vi) to provide the required benzodiazepine derivative.

The invention will now be further illustrated with the following specific, non-limiting examples. In these examples room temperature is denoted by r.t.

EXAMPLE 1

N-((3RS)-1-tert-Butycarbonylmethyl-2,3-dihydro-2-oxo-5-2-(1-methyl)imidazolyl)-1H-1,4-benzodiazepin-3-1-N'-3-methylphenyl urea
(Compound 3)

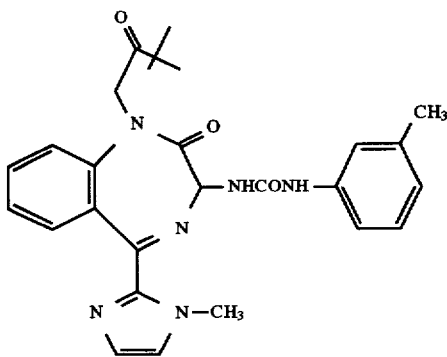

1A 2-Aminophenyl 1-methyl-2-imidazolyl ketone

The title compound was prepared according to the method of Fryer et al. (*Synth Commun* 1993, 23, 985) and was isolated as yellow needles (1.72 g, 85%) from DCM/hexane (m.p. 88°–90° C.; Lit. 91°–92° C.).

1B 2-(1-Benzotriazolyl)-2-benzyloxycarbonylamino acetic acid

The title compound was prepared according to the method of Katritsky (*J Org Chem* 1990, 55, 2206) in 81% yield.

1C (3RS)-Benzyloxycarbonylamino-2,3-dihydro-5-(2-(1-methyl)imidazolyl)-1H-1,4-benzodiazepin-2-one The amino ketone of example 1A (1.015 g, 5 mmol) and the benzotriazole derivative of example 1B (2.28 g, 7 mmol)

were suspended in DCM (20 ml) at 0° C. and treated portionwise with water soluble carbodiimide (1.34 g, 7 mmol) and DMAP (100 mg). The mixture was allowed to warm to r.t. over ½ h and then poured into 5% KHCO₃ and extracted with EtOAc (2×50 ml). The combined extracts were washed with brine, dried over Na₂SO₄ and evaporated. The residue was chromatographed on silica (eluant 75/25, v/v, EtOAc/hexanes) to provide a yellow foam (2.20 g, 86%) which was taken up in an ice-cold saturated solution of ammonia in methanol (30 ml), stoppered and stirred at r.t. for 1 h. The mixture was then evaporated and treated with a 10% solution of ammonium acetate in acetic acid at r.t. 1 h. The resultant mixture was evaporated and the residue partitioned between EtOAc and 1M NaOH. The organic portion was filtered (Whatman 1PS phase separator) and evaporated and the product crystallised as a white solid from EtOAc/hexane (905 mg, 47% overall).

¹H NMR (270 MHz, CDCl₃) δ 9.94 (1H, br.s.); 7.5–7.0 (m, 10H); 6.68 (2H, m); 5.2–5.0 (3H, m); 3.92 (3H, s) ppm.

1D (3RS)-Benzyloxycarbonylamino-1-tert-butylcarbonylmethyl-2,3-dihydro-5-(2-(1-methyl)imidazolyl)-1H-1,4-benzodiazepin-2-one The benzodiazepine of example 1D (850 mg, 2.174 mmol) was taken up in dry DMF (8 ml) at 0° C. under N₂. The solution was treated with NaH (85 mg, 80% disp. in. oil, 1.3 eq) with stirring for 1 h. 1-Bromopinacolone (506 mg, 1.3 eq) was added and stirring continued at r.t. 1 h. The mixture was evaporated and the residue partitioned between brine and EtOAc. The organic portion was filtered (Whatman 1 PS, phase separator) and evaporated. The residue was chromatographed on silica gel (eluant EtOAc) and crystallised from EtOAc/hexanes (610 mg, 58%).

¹H NMR (270 MHz, CDCl₃) δ 7.62 (1H, m); 7.50 (1H, m); 7.4–7.0 (9H, m); 6.64 (1H, d, J=8 Hz); 5.41 (1H, d, J=8 Hz); 5.16 (2H, s); 5.02 (1H, d, J=17 Hz); 4.32 (1H, d, J=17 Hz); 3.93 (3H, s); 1.22 (9H, s) ppm.

1E (3RS)-3-Amino-1-tert-butylcarbonylmethyl-2,3-dihydro-5-(2-(1-methyl)imidazolyl)-1H-1,4-benzodiazepin-2-one The benzodiazepine of example 1D was dissolved in DCM (20 ml) at 0° C. The solution was saturated with dry HBr gas, stoppered and stirred at 0° C. for 2 h. The mixture was evaporated and partitioned between 1M HCl and ether. The aqueous portion was basified and extracted with CHCl₃ (3×50 ml). The chloroform extracts were filtered (Whatman 1PS paper) and evaporated to provide a pale yellow foam (420 mg, 96%).

¹H NMR (270 MHz, CDCl₃) δ 7.62 (1H, m); 7.48 (1H, m); 7.26 (1H, m); 7.1–7.0 (3H, m); 5.08 (1H, d, J=16 Hz); 4.61 (1H, s); 4.29 (1H, d, J=16 Hz); 4.02 (3H, s); 2.37 (2H, br.s.); 1.25 (9H, s) ppm.

1F N-((3RS)-1-tert-Butylcarbonylmethyl-2,3-dihydro-2-oxo-5-(2-(1-methyl)imidazolyl)-1H-1,4-benzodiazepin-3-yl)-N'-(3-methylphenyl)urea The benzodiazepine of example 1E (210 mg, 0.5915 mmol) was dissolved in DCM (3 ml) and treated with m-tolyl isocyanate (85 µl, 0.65 mmol) at r.t. 1 h. The mixture was cooled to 0° C. and diluted with hexane (8 ml) and the resultant precipitate collected to provide the title compound (250 mg, 87%).

¹H NMR (270 MHz, CD₃OD) δ 7.7–7.1 (9H, m); 6.80 (1H, d, J=8.5 Hz); 5.48 (1H, s); 5.08 (1H, d, J=16.5 Hz); 4.81 (1H, d, J=16.5 Hz); 3.94 (3H, s); 2.28 (3H, s); 1.25 (9H, s) ppm.

M.S. (+ve FAB) [M+H]⁺=487.4.

EXAMPLE 2

N-((3RS)-1-tert-Butylcarbonylmethyl-2,3-dihydro-2-oxo-5-(2-(1-methyl)imidazolyl)-1H-1,4-benzodiazepin-3-yl)-N'-(3-dimethylammophenyl)urea

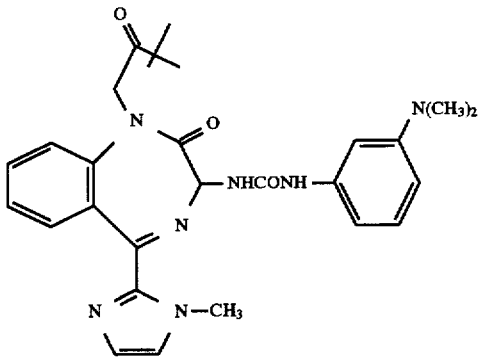

The benzodiazepine of example 1E (210 mg, 0.5915 mmol) was added as a solution in DCM (5 ml), to a mixture of m-(dimethylamino)benzoic acid (305 mg), triethylamine (360 µl) and diphenylphosphoryl azide (0.71 g), that had been heated under reflux under nitrogen for 5 h, then evaporated. The resultant mixture was stirred at r.t. 2 h, then evaporated and chromatographed (eluant EtOAc→6% MeOH/EtOAc). The product was recrystallised from MeCN to provide a colourless solid (254 mg, 83%).

¹H NMR (270 MHz, CDCl₃) δ 7.63 (1H, d, J =8 Hz); 7.48 (1H, m); 7.3–6.9 (8H, m); 6.42 (2H, m); 5.61 (1H, d, J=7.5 Hz); 4.95 (1H, d, J=17.7 Hz); 4.28 (1H, d, J=17.7 Hz); 3.96 (3H, s); 2.90 (6H, s); 1.22 (9H, s) ppm.

M.S. (+ve FAB) [M+H]⁺=516.5.

EXAMPLE 3

N-((3RS)-1-tert-Butylcarbonylmethyl-2,3-dihydro-2-oxo-5-(2-thiazolyl)-1H-1,4-benzodiazepin-3-yl)-N'-(3-methylphenyl)urea (Compound 1)

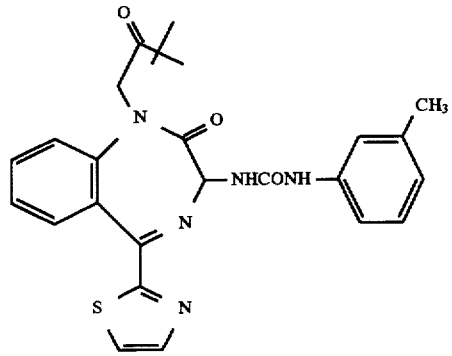

3A 2-Aminophenyl 2-thiazolyl-ketone

This was prepared over three steps following the method of Kaish et al. (*J Heterocyclic Chem* 1975, 12, 49).

3B (3RS)-Benzyloxycarbonylamino-2,3-dihydro-5-(2-thiazolyl)-1H-1,4-benzodiazeodiazepin-2-one This was prepared following the method of example 1C using 2-aminophenyl 2-thiazolyl ketone (2.04 g, 10 mmol). The product was afforded as pale yellow crystals after crystallisation with EtOAc (1.96 g, 50%).

¹H NMR (270 MHz, CDCl₃) δ 8.20 (1H, s); 8.00 (2H, m); 7.70–7.30 (9H, m); 6.70 (1H, d, J=8 Hz); 5.55 (1H, d, J=8 Hz); 5.25 (2H, s).

3C (3RS)-Benzyloxycarbonylamino-1-tert-butylcarbonylmethyl-2,3-dihydro-5-(2-triazolyl)-1H-1,4-benzodiazepin-2-one The title compound was prepared from the benzodiazepine of example 3B (1.96, 5 mmol) following the method of example 1D. The resultant product was purified by flash chromatography on silica gel (eluant 50% EtOAc-hexane Fr.) to afford the title compound as a pale yellow solid (2.00 g, 82%).

¹H NMR (270 MHz, CDCl₃) δ 7.80–7.05 (11H, m); 6.55 (1H, d, J=8 Hz); 5.45 (1H, d, J=8 Hz); 5.05 (2H, s); 4.95 (1H, d, J=17 Hz); 4.35 (1H, d, J=17 Hz); 1.20 (9H, s).

3D (3RS)-3-Amino-1-tert-butylcarbonylmethyl-2,3-dihydro-5-(2-thiazolyl)-1H-1,4-benzodiazepin-2-one The title compound was prepared using the benzodiazepine of example 3C (1.00 g, 2.04 mmol) following the method of example 1E. After work-up the resultant yellow solid was used without further purification (300 mg, 41%).

¹H NMR (270 MHz, CDCl₃) δ 7.70–7.05 (6H, m); 5.00 (1H, d, J=17 Hz); 4.65 (1H, s); 4.35 (1H, d, J=17 Hz); 2.40 (2H, s); 1.20 (9H, s).

3E N-((3RS)-1-tert-Butylcarbonylmethyl-2,3-dihydro-2-oxo-5-(2-thiazolyl)-1H-1,4-benzodiazepin-3-yl)-N'-(3-methylphenyl)urea The title compound was prepared following the method of example 1F from the benzodiazepine of example 3D (150 mg, 0.42 mmol) and m-tolyl isocyanate (77 μl, 0.6 mmol) in DCM. By adding hexane Fr. to the reaction mixture the title compound was afforded as pale yellow crystals (127 mg, 62%).

¹H NMR (270 MHz, CDCl₃) δ 7.75–7.10 (10H, m); 7.60 (1H, d, J=8 Hz); 6.65 (1H, d, J=8 Hz); 6.00 (1H, d, J=8 Hz); 5.00 (1H, d, J=17 Hz); 4.35 (1H, d, J=17 Hz); 2.30 (3H, s); 1.25 (9H, s).

M.S. (+ve FAB) [M+H]⁺=490.3.

EXAMPLE 4

N-((3RS)-1-tert-Butylcarbonylmethyl-2,3-dihydro-2-oxo-5-(2-thiazolyl)-1H-1,4-benzodiazepin-3-yl)-N'-(3-dimethylaminophenyl)urea (Compound 2)

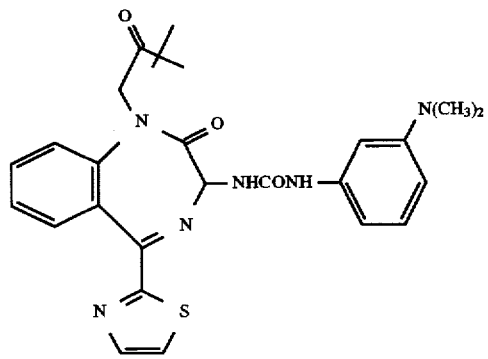

The title compound was prepared following the method of example 2 from the benzodiazepine of example 3D (150 mg, 0.42 mmol). The crude product was purified by flash chromatography on silica gel (eluant 75% EtOAc-hexane Fr.) and crystallised from acetonitrile to afford the title compound as a pale yellow solid (80 mg, 37%).

¹H NMR (270 MHz, CDCl₃) δ 8.00–7.10 (10H, m); 6.62 (1H, d, J=8 Hz); 6.58 (1H, d, J=8 Hz); 5.95 (1H, d, J=8 Hz); 5.05 (1H, d, J=17 Hz); 4.55 (1H, d, J=17 Hz); 3.05 (6H, s); 1.35 (9H, s).

M.S. (+ve FAB) [M+H]⁺=519.3.

EXAMPLE 5

N-((3RS)-1-tert-Butylcarbonylmethyl-2,3-dihydro-2-oxo-5-(2-pyrazinyl)-1H-1,4-benzodiazepin-3-yl)-N'-(3-methylphenyl)urea (Compound 17)

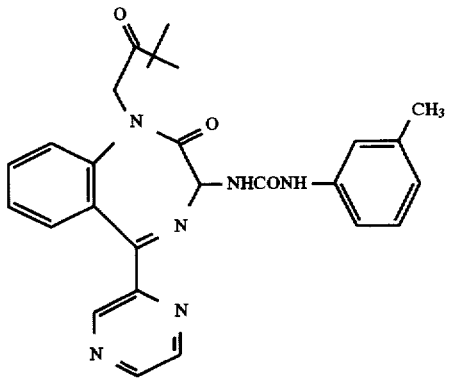

5A Phenacyl pyrazine

Phenacyl pyrazine was prepared from methyl pyrazine and methyl benzoate as described by Behun and Levine (*J Am Chem Soc* 1959, 81, 5157) in 68% isolated yield (chromatography on silica-eluant 60% EtOAc in hexanes).

5B 2-Phenyl-3-pyrazinyl indole

The ketone of example 5A (3.62 g, 18.4 mmol) and freshly distilled phenyl hydrazine (1.9 ml, 18.4 mmol) were stirred together in refluxing toluene under Dean-Stark conditions for 1 h, after which time no ketone remained as evidenced by t.l.c. Zinc (II) chloride (272 mg, 2 mmol) was added and reflux continued for 3 h. The mixture was evaporated and partitioned between EtOAc and brine and the organic portion filtered (Whatman 1PS phase separator) and evaporated. The residue was chromatographed on silica gel (eluant 45% EtOAc in hexanes) to provide the title compound as a fluffy tan solid (2.0 g, 40%).

¹H NMR (270 MHz, CDCl₃) δ 9.45 (1H, br.s.); 8.52 (1H, t, J=1.5 Hz); 8.43 (1H, d, J=1.5 Hz); 8.23 (1H, d, J=1.5 Hz); 8.10 (1H, m); 7.4–7.2 (8H, m) ppm.

5C 2-Amino benzoyl pyrazine

The indole of example 5B (813 mg, 3 mmol) was treated with CrO₃ in acetic acid as described for the 3-pyridyl analogue by Ockenden and Schofield (*J Chem Soc* 1953, 3440), to provide the benzyl amide of the title compound in 40% yield (isolated by chromatography-eluant 55% EtOAc in hexanes). The product (370 mg, 1.22 mmol) was taken up in ethanol (4 ml) and treated with 5M KOH (10 ml) at 70° C. for 4 h. The mixture was diluted with brine (50 ml) and extracted with CHCl₃ (×3). The combined extracts were filtered (Whatman 1PS, phase separator), evaporated and chromatographed on silica gel (eluant 40% EtOAc in hexanes) to provide the title compound as a yellow crystalline solid (120 mg, 60%).

¹H NMR (270 MHz, CDCl₃) δ 9.02 (1H, d, J=1.7 Hz); 8.71 (1H, d, J=1.7 Hz); 8.65 (1H, t, J=1.7 Hz); 7.63 (1H, dd, J₁=8 Hz, J₂=1.5 Hz); 7.33 (1H, dt, J_f=8 Hz, J_d=1.5 Hz); 6.75 (1H, d, J=8 Hz); 6.61 (1H, dt, J_f=8 Hz, J_d=1.5 Hz); 6.40 (2H, br.s.) ppm.

5D (3RS)-3-Benzyloxycarbonylamino-2,3-dihdro-5pyrazin-1H-1,4-benzodiazepin-2-one The title compound was prepared from the amino ketone of example 5C and the benzotriazole derivative of example 1B as described in example 1C. The product was isolated by chromatography on silica gel (eluant 85% EtOAc in hexanes) in 58% yield.

¹H NMR (270 MHz, CDCl₃) δ 9.78 (1H, br.s.); 9.28 (1H, d, J=1.5 Hz); 8.61 (1t, J=1.5 Hz); 8.55 (1H, d, J=1.5 Hz); 7.5–7.1 (8H, m); 7.06 (1H, d, J=8 Hz); 6.90 (1H, d, J=8 Hz); 5.40 (1H, d, J=8 Hz); 5.18 (2H, s).

5E (3RS)-3-Benzyloxcarbonylamino-1-tert-butylcarbonylmethyl-2,3-dihydro-5-pyrazinyl-1H-1,4-benzodiazepin-2-one The benzodiazepine of example 5D (120 mg, 0.31 mmol) was taken up in dry DMF (4 ml) at 0° C. under nitrogen. Sodium hydride (13 mg, 80% disp. in oil) was added to the stirring mixture followed after 45 min. by 1-bromopinacolone. The mixture was stirred at r.t. 1 h, evaporated and chromatographed on silica gel (eluant, 75% EtOAc in hexanes) to provide a colourless film (146 mg, 97%).

¹H NMR (270 MHz, CDCl₃) δ 9.37 (1H, d, J=1.3 Hz); 8.64 (1H, d, J=1.3 Hz); 8.55 (1H, t, J=1.4 Hz); 7.6–7.2 (8H, m); 7.14 (1H, d, J=8 Hz); 6.74 (1H, d, J=8 Hz); 5.55 (1H, d, J=8 Hz); 5.14 (2H, s); 4.95 (1H, d, J=16 Hz); 4.66 (1H d, J=16 Hz); 1.23 (9H, s) ppm.

5F (3RS)-3-Amino-1-tert-Butylcarbonylmethyl-2,3-dihydro-5-pyrazinyl-1H-1,4-benzodiazepin-2-one The benzodiazepine of example 5E was deprotected using HBr in DCM as described in example 1E. The brown oil product was not homogeneous but was used without purification in the next reactions.

5G N-((3RS)-1-tert-Butylcarbonylmethyl-2,3-dihydro-2-oxo-5-(2-pyrazinyl)-1 H-1,4-benzodiazepin-3-yl)-N'-(3-methylphenyl)urea The title compound was prepared from the benzodiazepine of example 5F (0.15 mmol), by treating a DCM solution (3 ml) with m-tolyl isocyanate at 0° C. After 1 h, the mixture was evaporated and chromatographed on silica gel (eluant 75% EtOAc→90% EtOAc in hexanes) to provide a colourless solid (44 mg, 61% for two steps).

¹H NMR (270 MHz, CDCl₃) δ 9.37 (1H, d, J =1 Hz); 8.62 (1H, d, J=1.5 Hz); 8.54 (1H, t, J=1.5 Hz); 7.54 (1H, t, J=8 Hz); 7.4–7.0 (8H, m); 6.82 (1H, d, J=7 Hz); 5.77 (1H, d, J=8 Hz); 4.89 (1H, d, J=18 Hz); 4.66 (1H, d, J=18 Hz); 2.26 (3H, s); 1.20 (9H, s) ppm.

M.S. (+ve FAB) [M+H]⁺=485.2.

EXAMPLE 6

N-((3RS)-1-tert-Butylcarbonylmethyl-2,3-dihydro-2-oxo-5-(2-pyrazinyl)-1H-1,4-benzodiazepin-3-yl)-N'-(3-dimethylaminophenyl)urea (Compound 18)

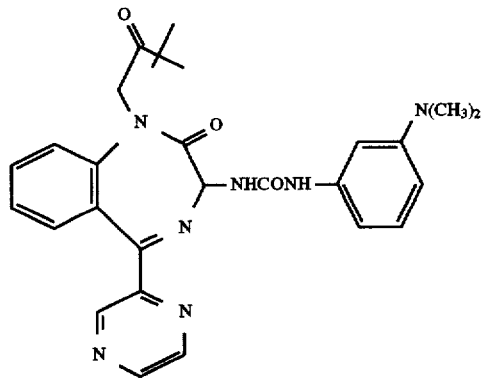

The title compound was prepared as described in example 2 from the benzodiazepine of example 5F, it was purified by chromatography on silica gel (eluant 80% EtOAc/hexanes→100% EtOAc) to provide a colourless solid (34 mg, 44%).

¹H NMR (270 MHz, CDCl₃) δ 9.37 (1H, d, J=1.5 Hz); 8.62 (1H, d, J=1.5 Hz); 8.54 (1H, t, J=1.5 Hz); 7.50 (1H, dt, J₁=8 Hz, J_d=1.5 Hz); 7.4–7.0 (6H, m); 6.89 (1H, m); 6.51 (1H, d, J=8 Hz); 6.43 (1H, d, J=8 Hz); 5.77 (1H, d, J=8 Hz); 4.87 (1H, d, J=17.5 Hz); 4.63 (1H, d, J=17.5 Hz); 2.90 (6H, s); 1.19 (9H, s) ppm.

M.S. (+ve FAB) [M+H]⁺=514.3.

EXAMPLE 7

N-((3RS)-1-tert-Butylcarbonylmethyl-2,3-dihydro-5-(2-imidazolyl)-2-oxo-1H-1,4-benzodiazepin-3-yl-N'-(3-methylphenyl)urea (Compound 5)

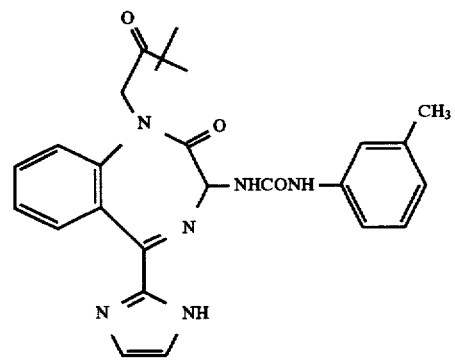

7A 2-(Hydroxy-(2-nitrophenyl))methyl-N,N-dimethylimidazole-1-sulphonamide

N,N-Dimethylimidazole-1-sulphonamide (Chadwick & Ngochindo, *J Chem Soc Perkin Trans I* 1984, 481) (4.0 g, 23.2 mmol) was taken up in dry THF (40 ml) at −70° C. under nitrogen. n-Butyl lithium (16 ml, 1.6M solution in hexanes) was added dropwise and the mixture stirred at −70° C. for 20 min. 2-Nitrobenzaldehyde (5.6 g, 37 mmol) was added in THF (20 ml) and the mixture allowed to warm to r.t. over 2 h. The mixture was evaporated and partitioned between 5% KHCO₃ and EtOAc. The organic portion was washed with brine, filtered (Whatman 1PS, phase separator), evaporated and chromatographed on silica gel (eluant 85% EtOAc in hexanes) to provide the title compound as a yellow foam (3.31 g, 44%).

$^1$H NMR (270 MHz, CDCl$_3$) δ 8.10 (1H, d, J=8 Hz); 7.95 (1H, d, J=8 Hz); 7.72 (1H, t, J=8 Hz); 7.54 (1H, t, J=8 Hz); 7.21 (1H, s); 6.85 (1H, s); 6.80 (1H, d, J=2 Hz); 4.45 (1H, d, J=2 Hz); 3.02 (6H, s) ppm.

7B 2-(2-Nitrobenzoyl)imidazole

The sulphonamide of example 7A (3.30 g, 10.12 mmol) was taken up in glacial acetic acid (50 ml) at 60° C. under nitrogen. Chromium trioxide (2 g) was added and the mixture stirred at 100° C. for ½ h, then cooled to r.t. The residue was poured into 1M KOH (500 ml) and extracted with EtOAc (2×100 ml). The combined extracts were washed with brine, filtered (Whatman 1PS, phase separator) and evaporated. The product was crystallised from EtOAc/hexanes as a pale green solid (1.72 g, 77%)and was used without further purification.

$^1$H NMR (270 MHz, CD$_3$OD) δ 8.30 (1H, d, J=7 Hz); 8.0–7.7 (3H, m); 7.53 (1H, br.s.); 7.24 (1H, br.s.) ppm.

7C 2-(2-Nitrobenzoyl)-1-((2-(trimethylsilyl)ethoxy)methyl)imidazole

The imidazole of example 7B (1.70 g, 7.83 mmol) was dissolved in dry DMF (15 ml) at 0° C. under nitrogen. Sodium hydride (260 mg, 80% disp. in oil, 8.6 mmol) was added portionwise with stirring and the mixture stirred at r.t. 1 h. [2-(trimethylsilyl)ethoxy]methyl chloride (1.5 g, 8.6 mmol) and stirring continued at r.t. for 3 h. The mixture was evaporated and partitioned between 5% KHCO$_3$ and EtOAc. The organic portion was washed with brine, evaporated and chromatographed on silica gel (eluant 45% EtOAc in hexanes) to provide the title compound as a colourless oil (1.51 g, 56%).

$^1$H NMR (270 MHz, CDCl$_3$) δ 8.14 (1H, d, J=8 Hz); 7.8–7.6 (3H, m); 7.34 (1H, s); 7.11 (1H, s); 5.97 (2H, s); 3.67 (2H, m); 0.96 (2H, m); 0.00 (9H, s) ppm.

7D 2-(2-Aminobenzoyl)-1-((2-(trimethylsilyl)ethoxy)methyl)imidazole

The nitro-compound of example 7C (1.50 g, 4.32 mmol) was dissolved in dry THF (60 ml) and the solution degassed and charged with 5% Pd.-on-carbon (800 mg). The mixture was hydrogenated on a Parr apparatus at 30 psi and r.t. for 2 h, then filtered (celite) and evaporated. The resultant yellow oil was chromatographed on silica gel (eluant 40% EtOAc in hexanes) to provide the pure title compound (1.15 g, 84%).

$^1$H NMR (270 MHz, CDCl$_3$) δ 8.38 (1H, d, J=8 Hz); 7.35 (3H, m); 6.77 (2H, m); 6.20 (2H, br.s.); 5.75 (2H, s); 3.60 (2H, m); 0.96 (2H, m); 0.00 (9H, s) ppm.

7E (3RS)-Benzyloxycarbonylamino-2,3-dihydro-5-(2-(1-((2-trimethylsilyl)ethoxy)methyl))imidazolyl)-1H-1,4-benzodiazepin-2-one The amino ketone of example 7D (1.10 g, 3.47 mmol) was convened to the title compound by the method described in example 1C. The product was crystallised from EtOAc/hexanes to provide a colourless solid (720 mg, 41%).

$^1$H NMR (270 MHz, CDCl$_3$) δ 9.63 (1H, br.s.); 7.6–7.2 (10H, m); 6.78 (1H, d, J=8 Hz); 6.67 (1H, d, J=8 Hz); 5.90 (1H, d, J=11 Hz); 5.63 (1H, d, J=11 Hz); 5.2 (3H, m); 3.60 (2H, m); 0.96 (2H, m); 0.00 (9H, s) ppm.

7F (3RS)-Benzyloxycarbonylamino-1-tert-butylcarbonylmethyl-2,3-dihydro-5-(2-(1-((2-(trimethylsilyl)ethoxy)methyl))imidazolyl)-1H-1,4-benzodiazepin-2-one The benzodiazepine of example 7E (505 mg, 1 mmol) was alkylated with 1-bromopinacolone as described in example 1D. The product was purified by column chromatography on silica gel (eluant 75% EtOAc in hexanes) to provide a pale yellow oil (420 mg, 70%).

$^1$H NMR (270 MHz, CDCl$_3$) δ 7.63 (1H, dd, J$_1$=8 Hz, J$_2$=1.5 Hz); 7.52 (1H, m); 7.4–7.3 (7H, m); 7.18 (1H, s); 7.07 (1H, d, J=8 Hz); 6.71 (1H, d, J=7.5 Hz); 5.91 (1H, d, J=10 Hz); 5.67 (1H, d, J=10 Hz); 5.43 (1H, d, J=7.5 Hz 5.15 (2H, s); 5.06 (1H, d, J=18 Hz); 4.36 (1H, d, J=18 Hz); 3.60 (2H, m); 1.28 (9H, s); 0.95 (2H, m); 0.00 (9H, s) ppm.

7G N-((3RS)-1-tert-Butylcarbonylmethyl-2,3-dihydro-2-oxo-5-(2-(1-((2-trimethylsilyl)ethoxy)methyl))imidazolyl)-1H-1,4-benzodiazepin-3-yl)-N'-(3-methylphenyl)urea The benzodiazepine of example 7F (95 mg, 0.157 mmol) was dissolved in ethanol/acetic acid (95/5, v/v, 5 ml). The mixture was degassed and 5% Pd.-on-carbon (40 mg) added. The mixture was hydrogenated at atmospheric pressure and room temp. for 45 min, then filtered (celite filter aid), evaporated and azeotroped twice with toluene. The residue was taken up in DCM (2 ml) and m-tolyl isocyanate (24 μl, 0.19 mmol) added. The resultant mixture was stirred at r.t. 1 h, then evaporated and chromatographed on silica gel (eluant 80% EtOAc in hexanes) to provide the title compound as a colourless solid (69 mg, 73%).

$^1$H NMR (270 MHz, CDCl$_3$) δ 7.63 (1H, d, J=8 Hz); 7.55 (1H, t, J=8 Hz); 7.4–7.0 (9H, m); 6.86 (1H, d, J=7.2 Hz); 5.97 (1H, d, J=10.5 Hz); 5.73 (1H, d, J=10.5 Hz); 5.63 (1H, d, J=7.2 Hz); 4.94 (1H, d, J=18 Hz); 4.28 (1H, d, J=18 Hz); 3.67 (2H, m); 2.31 (3H, s); 1.26 (9H, s); 0.96 (2H, m); 0.00 (9H, s) ppm.

7H N-((3RS)-1-tert-Butylcarbonylmethyl-2,3-dihydro-2-oxo-5-(2-imidazolyl)-1H-1,4-benzodiazepin-3-yl)-N'-(3-methylphenyl)urea The benzodiazepine of example 7G (69 mg, 0.1146 mmol) was taken up in ethanol (8 ml) and conc. HCl (2 ml) added. The mixture was heated at 70° C. for 1 h and then cooled and evaporated. The residue was partitioned between 1M HCl and ether. The aqueous portion was basified and extracted with EtOAc (×3). The combined extracts were filtered (Whatman 1PS, phase separator) and evaporated. The residue was chromatographed on silica gel (eluant EtOAc) and then further purified by MPLC on reverse-phase (C$_{18}$, eluting with a gradient of 20% MeCN in water to 100% MeCN) to provide a colourless solid (5 mg, 9%).

$^1$H NMR (270 MHz, CDCl$_3$) δ 8.07 (1H, d, J=8 Hz); 7.6–6.9 (10H, m); 6.63 (1H, d, J=7 Hz); 5.62 (1H, d, J=7 Hz); 5.41 (1H, d, J=17 Hz); 4.20 (1H, d, J=17 Hz); 2.18 (3H, s); 1.25 (9H, s).

EXAMPLE 8

N-((3RS)-1-tert-Butylcarbonylmethyl-2,3-dihydro-5-(2-imidazolyl)-2-oxo-1H-1,4-benzodiazepin-3-yl)-N'-(3-dimethylaminophenyl)urea

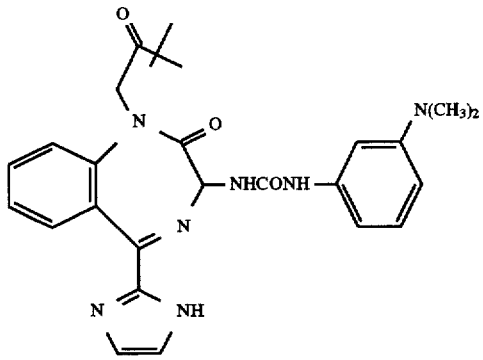

8A N-((3RS)-1-tert-Butylcarbonylmethyl-2,3-dihydro-5-(2-(1-((2-trimethylsilyl)ethoxy) methyl))imidazolyl)-2-oxo-1H-1,4-benzodiazepin-3-yl)-N'-(3-dimethylaminophenyl) urea (Compound 6)

The benzodiazepine of example 7F (140 mg, 0.232 mmol) was taken up in ethanol/acetic acid (95/5, v/v, 8 ml). The solution was degassed and then charged with 5% Pd.-on-carbon (60 mg). The mixture was hydrogenated at ambient temperature and pressure for 45 min, then filtered (celite filter aid), evaporated and azeotroped with toluene (×2). The resultant amine was taken up in DCM and treated with an excess of 3-(dimethylamino)phenyl isocyanate (prepared by refluxing a mixture of 3-dimethylaminobenzoic acid (120 mg), triethylamine (147 µl) and diphenylphosphoryl azide (280 mg) in benzene under $N_2$ for 3 h) at r.t. 4 h. The mixture was evaporated and chromatographed on silica gel (eluant 90% EtOAc in hexanes →EtOAc) to provide a colourless solid (106 mg, 72%).

$^1$H NMR (270 MHz, CDCl$_3$) δ 7.65 (1H, d, J=8 Hz); 7.54 (1H, t, J=8 Hz); 7.36–7.23 (4H, m); 7.12–7.05 (3H, m); 6.91 (1H, m); 6.51–6.43 (2H, m); 5.95 (1H, d, J=10.6 Hz); 5.76 (1H, d, J=10.6 Hz); 5.63 (1H, d, J=8 Hz); 4.95 (1H, d, J=17.8 Hz); 4.22 (1H, d, J=17.8 Hz); 3.66 (2H, m); 2.95 (6H, s); 1.26 (9H, s); 0.95 (2H, m); 0.00 (9H, s) ppm.

8B N-((3RS)-1-tert-Butylcarbonylmethyl-2,3-dihydro-5-(2-imidazolyl)-2-oxo-1H-1,4-benzodiazepin-3-yl)-N'-(3-dimethylaminophenyl)urea The benzodiazepine of example 8A (106 mg, 0.168 mmol) was dissolved in dry DCM (20 ml) and the solution cooled to 0° C. Dry HBr gas was bubbled slowly through the mixture at 0° C. for ½ h. The mixture was stoppered and sitting continued for a further ½ h at 0° C.

The mixture was then degassed and evaporated. The residue was partitioned between 1M KOH and EtOAc. The organic portion was washed with brine, filtered (Whatman 1PS, phase separator) and evaporated. The product was chromatographed on silica gel (eluant 2% MeOH in EtOAc) and the title compound isolated as a colourless solid by freeze drying from acetonitrile-water (48 mg, 60%).

$^1$H NMR (270 MHz, CDCl$_3$) δ 8.11 (1H, d, J=8 Hz); 7.62 (1H, t, J=8 Hz); 7.48–7.31 (3H, m); 7.05–6.93 (4H, m); 6.70 (1H, br.s.); 6.32 (1H, d, J=8 Hz); 6.27 (1H, br.d.); 5.73 (1H, d, J=7.4 Hz); 5.40 (1H, d, J=17.5 Hz); 4.48 (1H, d, J=17.5 Hz); 2.89 (6H, s); 1.16 (9H, s) ppm.

M.S. (+ve FAB) [M+H]$^+$=502.3

EXAMPLE 9

N-((3RS)-1-tert-Butylcarbonylmethyl-2,3-dihydro-5-(2-imidazolyl)-2-oxo-1H-1,4-benzodiazepin-3-yl)-N'-(3-(1-pyrrolidyl)phenyl)urea (Compound 19)

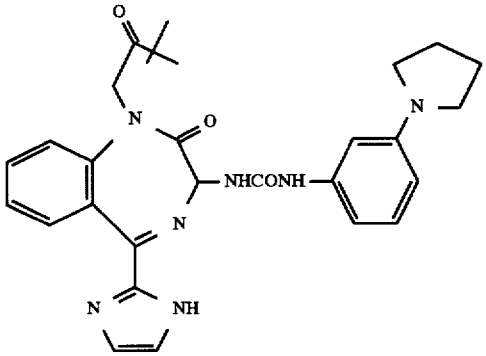

9A 3-(1-Pyrrolidyl)benzoic acid m-Amino benzoic acid (13.7 g, 0.1 mol) was taken up in methanol (150 ml) and cooled to 0° C. Acetyl chloride (10 ml) was added dropwise, and then the mixture heated until reflux, under nitrogen for 14 h. The mixture was cooled, evaporated and partitioned between EtOAc and 5% KHCO$_3$. The organic portion was washed with brine, filtered (Whatman 1PS, phase separator) and evaporated to provide a brown oil which crystallised on standing (13.2 g, 88%). A portion of the amino ester (5.45 g, 36.1 mmol) was taken up in dry DMF (70 ml) and treated with sodium hydride (3.78 g, 80% disp. in oil, 126 mmol) at 0° C. under nitrogen for 1½ h. 1,4-dibromobutane (14.05 g, 65 mmol) and potassium iodide (0.6 g, 3.7 mmol) were added and the mixture heated at 80° C. for 72 h. The mixture was cooled, evaporated and partitioned between EtOAc and 5% KHCO$_3$. The organic portion was washed with brine, filtered (Whatman 1PS, phase separator) and evaporated. The residue was chromatographed on silica (eluant 8% EtOAc/hexane) to provide a pale yellow solid (1.70 g, 23%). The solid was taken up in dioxan/water (40 ml) and treated with LiOH.7H$_2$O (1.75 g, 5 eq) at r.t. for 10 min, then at 40° C. for 30 min. Acetic acid (10 was added and the mixture was evaporated, azeotroped with toluene and crystallised from AcOH/water/dioxan to provide a pale brown solid (1.26 g, 80%) which was dried in vacuo over P$_2$O$_5$.

$^1$H NMR (270 MHz, CDCl$_3$) δ 7.4–7.2 (3H, m); 6.78 (1H, m); 3.35 (4H, m); 2.02 (4H, m) ppm.

9N-((3RS)-1-tert-Butylcarbonylmethyl-2,3-dihydro-5-(2-(1-((2-trimethylsilyl)ethoxy) methyl))imidazolyl)-2-oxo-1H-1,4-benzodiazepin-3-yl)-N'-(3-(1-pyrrolidyl)phenyl) urea The benzodiazepine of example 7F (140 mg, 0.232) was taken up in ethanol/acetic acid (95/5, v/v, 8 ml) and hydrogenated over 5% Pck-on-carbon (60 mg) at ambient pressure and temperature for 45 min. The mixture was filtered (celite, filter aid), evaporated and azeotroped with toluene (×2). The residue was taken up in DCM (4 ml) and treated with 3-(1-pyrrolidyl)phenyl isocyanate (prepared by refluxing a mixture of the acid of example 9A (140 mg), triethylamine (147 µl) and diphenylphosphoryl azide (280 mg) in benzene (10 ml) for 2 h) at r.t. 4 h. The mixture was evaporated and chromatographed on silica gel (eluant 90% EtOAc in hexanes→EtOAc) to provide a colourless solid (110 mg, 72%).

$^1$H NMR (270 MHz, CDCl$_3$) δ 7.65 (1H, dd, J$_1$=8 Hz, J$_2$=1.7 Hz); 7.54 (1H, dt, J,8 Hz, J$_d$=1.8 Hz); 7.4–7.0 (7H, m); 6.75 (1H, m); 6.43 (1H, d J=8 Hz); 6.31 (1H, d, J=8 Hz); 5.95 (1H, d, J=10.4 Hz); 5.75 (1H, d, J=10.4 Hz); 5.63 (1H, d, J=7.2 Hz); 4.96 (1H, d, J=17.8 Hz); 4.26 (1H, d, J=17.8 Hz); 3.63 (2H, m); 3.29 (4H, m); 2.00 (4H, m); 1.27 (9H, s); 0.95 (2H, m); 0.00 (9H, s) ppm.

9C N-((3RS)-1-tert-Butylcarbonylmethyl-2,3-dihydro-5-(2-imidazolyl)-2-oxo-1H-1,4-benzodiazepin-3-yl)-N'-(3-(1-pyrrolidyl)phenyl)urea The benzodiazepine of example 9B (110 mg, 0.1674 mmol) was deprotected with HBr as described in example 8B. The product was chromatographed on silica gel (eluant 2% MeOH in EtOAc) and freeze-dried from acetonitrile-water to provide a pale yellow solid (46 mg, 55%).

¹H NMR (270 Hz, CDCl₃) δ 8.11 (1H, d, J =7 Hz); 7.62 (1H, t, J=7 Hz); 7.47–7.2 (4H, m); 7.09–6.80 (4H, m); 6.23–6.13 (2H, m); 5.74 (1H, d, J=7.2 Hz); 5.36 (1H, d, J=17.5 Hz); 4.49 (1H, d, J=17.5 Hz); 3.21 (4H, m); 1.95 (4H m); 1.16 (9H, s) ppm.

M.S. (+ve FAB) [M+H]⁺=528.8.

EXAMPLE 10

N-((3RS)-1-tert-Butylcarbonylmethyl-2,3-dihydro-5-(4-imidazolyl)-2-oxo-1H-1,4-benzodiazepin-3-yl)-N'-(3-methylphenyl)urea (Compound 12)

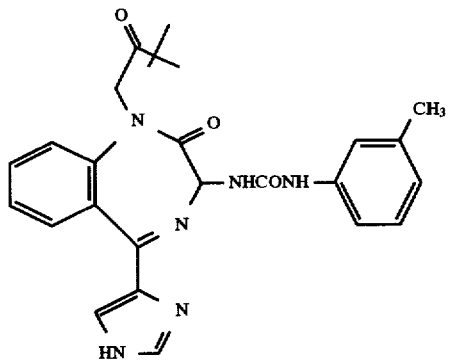

10A 5-(Hydroxy(2-nitrophenyl))methyl-N,N-dimethylimidazole-1-sulphonamide

N,N-Dimethylimidazole-1-sulphonamide (Chadwick and Ngochindo, J Chem Soc Perkin Trans I 1984, 481) (6.0 g, 34.8 mmol) was taken up in dry THF (150 ml) at –78° C. under nitrogen. n-Butyl lithium (24 ml, 1.6M solution in hexanes) was added dropwise and stirring continued at –78° C. for ½ h. Triethylchlorosilane (11.7 ml, 69.6 mmol) was then added and the mixture allowed to warm to r.t. and stirred overnight. The mixture was then evaporated at below 50° C. under high vacuum to remove all volatiles. The residue was redissolved in dry THF (100 ml) at –78° C. under nitrogen and treated dropwise with sec-butyl lithium (53 ml, 1.3M solution in cyclohexane). The mixture was stirred at –78° C. for 45 min, then a solution of o-nitrobenzaldehyde (10.5 g) added in the THF (40 ml). The mixture was allowed to warm to r.t. and stirred 22 h. The mixture was then evaporated and partitioned between 2M HCl (100 ml) and ether (150 ml). The aqueous portion was basified and extracted with EtOAc (×2). The combined extracts were filtered (Whatman 1PS, phase separator) and evaporated and the product crystallised from EtOAc/hexane to provide a pale yellow solid (3.86 g, 34%).

¹H NMR (270 MHz, CDCl₃) δ 8.13 (1H, d, J=8 Hz); 8.12 (1H, d, J=8 Hz); 7.92 (1H, d, J=1 Hz); 7.79 (1H, t, J=8 Hz); 7.57 (1H, t, J=8 Hz); 6.70 (1H, s 6.28 (1H, s); 3.08 (6H, s) ppm.

10B 4-(2-nitrobenzoyl)imidazole

The imidazole of example 10A (3.8 g, 11.66 mmol) was taken up in acetic acid (60 ml) at 40° C. Chromium trioxide (2.3 g) was added and the mixture heated at 100° C. for 1 h, then cooled and poured into ice-water. The mixture was basified and extracted with EtOAc (×3). The combined extracts were evaporated, azeotroped with toluene and the residue crystallised from EtOAc/hexane to provide an off-white solid (725 mg, 29%).

¹H NMR (270 MHz, CDCl₃) δ 7.81 (1H, d, J=7 Hz); 7.5–7.3 (5H, m); 3.25 (6H, s) ppm.

10C 4-(2-Nitrobenzoyl)-1-((2-trimethylsilyl)ethoxy) methyl)imidazole and 10D 5-(2-Nitrobenzoyl)-1-((2-trimethylsilyl)ethoxy) methyl)imidazole The imidazole of example 10B (700 mg, 3.226 mmol) was dissolved in dry DMF (15 ml) at 0° C. under nitrogen. Sodium hydride (106 mg, 80% disp. in oil) was added portionwise and the mixture stirred at 0° C.→r.t. over 1 h. [2-(Trimethylsilyl)ethoxy]methyl chloride (620 mg, 3.55 mmol) was added and stirring continued at r.t. 1 h. The mixture was then poured into 5% KHCO₃ and extracted with EtOAc. The extracts were washed with brine, filtered (Whatman 1PS, phase separator) and evaporated. The residue was chromatographed on silica gel (eluant 80% EtOAc in hexanes until removal of fast product then EtOAc) to provide two colourless oils. 10C was obtained in 29% yield (320 mg), the faster eluting isomer and 10D was obtained in 31% yield (350 mg), the slower eluting isomer.

10C ¹H NMR (270 MHz, CDCl₃) δ 8.15 (1H, d, J=7.5 Hz); 7.86 (1H, s); 7.78–7.58 (3H m); 7.53 (1H, s); 5.31 (2H, s); 3.52 (2H, m); 0.92 (2H, m); 0.00 (9H, s) ppm.

10D ¹H NMR (270 MHz, CDCl₃) δ 8.17 (1H, d, J=7.5 Hz); 7.91 (1H, s); 7.79–7.64 (2H, m); 7.53 (1H, dd, J₁=7.5 Hz, J₂=1.5 Hz); 7.18 (1H, s); 5.85 (2H, s); 3.70 (2H, m); 0.97 (2H, m); 0.00(9H, s) ppm.

10E 4-(2-Aminobenzoyly)-1-((2-trimethylsilyl)ethoxy)-imidazole

The imidazole of example 10C (320 mg, 0.922 mmol) was dissolved in dry THF (25 ml) and hydrogenated over 5% Pd.-on-carbon at 25 psi and r.t. for 2 h. The mixture was filtered (celite filter aid) and evaporated to provide a yellow oil (286 mg, 98%) which was used in the next reaction without further purification.

¹H NMR (270 MHz, CDCl₃) δ 8.42 (1H, dd., J₁=8.2 Hz, J₂=1.6 Hz); 7.69 (2H, m); 7.27 (1H, m); 6.70 (2H, m); 6.03 (2H, br.s.); 5.32 (2H, s); 3.54 (2H, m); 0.95 (2H, m); 0.00 (9H, s) ppm.

10F (3RS)-Benzyloxycarbonylamino-2,3-dihydro-5-(4-(1-((2-trimethylsilyl)ethoxy) methyl))-imidazolyl)-1H-1,4-benzodiazepin-2-one The imidazole of example 10E (286 mg, 0.902 mmol) was converted to the benzodiazepine title compound by the method described in example 1C. The product was chromatographed on silica gel (eluant 3% MeOH in EtOAc) to provide a pale yellow oil (300 mg, 66%).

¹H NMR (270 MHz, CDCl₃) δ 9.75 (1H, s); 7.66–7.13 (10H, m); 6.96 (1H, d, J=8 Hz); 6.62 (1H, d, J=8 Hz); 5.38–5.07 (5H, m); 3.52 (2H, t, J=8 Hz); 0.92 (2H, t, J=8 Hz); 0.130 (9H, s) ppm.

10G (3RS )-Benzyloxycarbonylamino-1-tert-butylcarbonylmethyl-2,3-dihydro-5-(4-(1-((2-(trimethylsilyl)ethoxy)methyl))-imidazolyl)-1H-1,4-benzodiazepin-2-one The benzodiazepine of example 10F (300 mg, 0.594 mmol) was alkylated with 1-bromopinacolone as described in example 1D. The product was chromatographed (eluant 2% MeOH in EtOAc) to provide a colourless foam (305 mg, 85%).

¹H NMR (270 MHz, CDCl₃) δ 7.68 (1H, d, J=7.6 Hz); 7.60 (1H, s); 7.49 (1H, t, J=7.6 Hz); 7.35–7.22 (6H, m); 7.05 (1H, d, J=8 Hz); 6.63 (1H, d, J=8 Hz); 5.46 (1H, d, J=8 Hz); 5.27 (2H, s); 5.10 (2H, m); 5.03 (1H, d, J=17.8 Hz); 4.38 (1H, d J=17.8 Hz); 3.51 (2H, t, J=8 Hz); 1.24 (9H, s); 0.92 (2H, t, J=8 Hz) 0.00 (9H, s) ppm.

10H N-3((RS)-1-tert-Butylcarbonylmethyl-2,3-dihydro-2-oxo-5-4-(1-((2(trimethylsilyl) ethoxy)methyl))-imidazol-1-H-1,4-benzodiazepin-3yl)-N'-(3-methylphenyl)urea The title compound was prepared from the benzodiazepine of example 10G (150 mg, 0.249 mmol) by the method described in example 7G. The product was chromatographed on silica gel (eluant EtOAc→5% MeOH in EtOAc) to provide a colourless solid (97 mg, 65%).

¹H NMR (270 MHz, CDCl₃) δ 7.77 (1H, s); 7.71 (1H, d, J=8 Hz); 7.62 (1H, s); 7.51 (1H, t, J=7 Hz); 7.33–6.93 (7H, m); 6.77 (1H, d, J=7 Hz); 5.70 (1H, d, J=8.2 Hz); 5.21 (2H, s); 4.87 (1H, d, J=17.8 Hz); 4.41 (1H, d, J=17.8 Hz); 3.51 (2H, t, J=7.5 Hz); 2.24 (3H, s); 1.20 (9H, s); 0.91 (2H, t, J=7.5 Hz); 0.00 (9H, s).

10I N-((3RS)-1-tert-Butylcarbonylmethyl-2,3-dihydro-2-oxo-5-(4-imidazolyl)-1H-1,4-benzodiazepin-3-yl)-N'-(3-methylphenyl)urea The title compound was prepared by treatment of the benzodiazepine of example 10H with HBr as described in example 8B, and the product crystallised from DCM/hexane to provide a white solid (44 mg, 58%).

¹HNMR (270 MHz, CDCl₃) δ 7.69 (1H, d, J=7 Hz); 7.56–7.19 (8H, m); 6.91–6.85 (3H, m); 6.86 (1H, d, J=7 Hz); 5.53 (1H, d, J=7 Hz); 5.22 (1H, br. d.); 4.41 (1H, d, J=17.5 Hz); 2.07 (3H, s); 1.06 (9H, s) ppm.

M.S. (+ve FAB) [M+H]⁺=473.3.

EXAMPLE 11

N-((3RS)-1-tert-Butylcarbonylmethyl-2,3-dihydro-2-oxo-5-(4-imidazolyl)-1H-1,4-benzodiazepin-3-yl)-N'-(3-dimethylaminophenyl)urea (Compound 8)

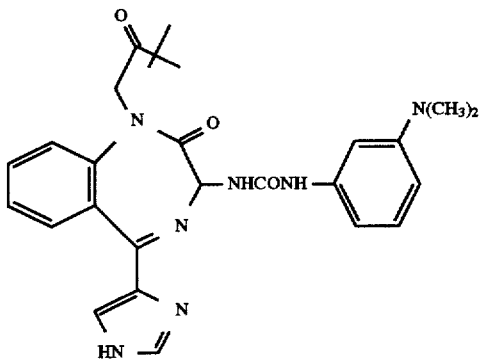

11A N-((3RS)-1-tert-Butylcarbonylmethyl-2,3-dihydro-2-oxo-5-(4-(1-((2-trimethylsilyl) ethoxy)methyl))-imidazol-yl)-1H-1,4-benzodiazepin-3-yl)-N'-(3-dimethylaminophenyl) urea The title compound was prepared from the benzodiazepine of example 10G (150 mg, 0.249 mmol) by the method described in example 8A. The product was chromatographed on silica gel (eluant EtOAc→5% MeOH in EtOAc) to provide a colourless solid (130 mg, 83%).

¹H NMR (270 MHz, CDCl₃) δ 7.78 (1H, s); 7.71 (1H, d, J=8 Hz); 7.65 (1H, s); 7.50 (1H, t, J=7 Hz); 7.38–7.25 (3H, m); 7.06–6.96 (2H, m); 6.89 (1H, s); 6.42–6.32 (2H, m); 5.70 (1H, d, J=8 Hz); 5.22 (2H, s); 4.85 (1H, d, J=17.8 Hz); 4.26 (1H, d, J=17.8 Hz); 3.51 (2H, t, J=8 Hz); 2.86 (6H, s); 1.20 (9H, s); 0.91 (2H, t, J=8 Hz); 0.00 (9H, s) ppm.

11B N-((3RS)-1-tert-Butylcarbonylmethyl-2,3-dihydro-2-oxo-5-(4-imidazolyl)-1H-1,4-benzodiazepin-3-yl)-N'-(3-dimethylaminophenyl)urea The title compound was prepared from the benzodiazepine of example 11A as described in example 8B. The product was crystallised from EtOAc/hexane to provide an off-white solid (69 mg, 70%).

¹H NMR (270 MHz, CDCl₃) δ 7.87 (1H, d, J=7.8 Hz); 7.71–7.03 (10H, m); 6.48–6.39 (2H, m); 5.71 (1H, d, J=7 Hz); 5.22 (1H, br.d.); 4.66 (1H, d, J=17.6 Hz); 2.92 (6H, s); 1.25 (9H, s) ppm.

M.S. (+ve FAB) [M+H]⁺=502.3.

EXAMPLE 12

N-((3RS)-1-(4-methylphenyl)carbonylmethyl-2,3-dihydro-2-oxo-5-(4-imidazolyl)-1H-1,4-benzodiazepin-3-yl)-N'-(3-methylphenyl)urea
(Compound 20)

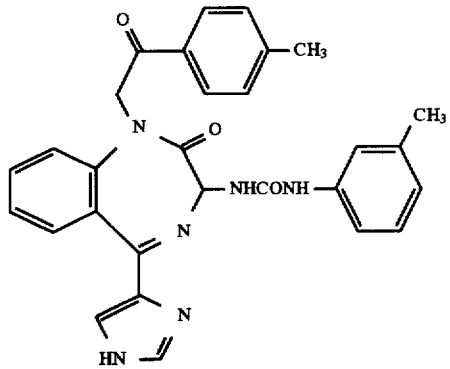

12A 5-(2-Aminobenzoyl)-1-((2-(trimethylsilyl)ethoxy)methyl)-imidazole

The imidazole of example 10D (350 mg, 1.009 mmol) was hydrogenated over 5% Pd.-on-carbon as described in example 10E. The yellow oil product (313 mg, 98%) was used in the next reaction without further purification.

¹H NMR (270 MHz, CDCl₃) δ 7.89 (1H, s); 7.81 (1H, dd, J₁=8 Hz, J₂=1.6 Hz); 7.53 (1H, s); 7.34 (1H, dr, J₁=8 Hz, J₂=1.6 Hz); 6.77–6.68 (2H, m); br.s.); 5.77 (2H, s); 3.62 (2H, m); 0.96 (2H, m); 0.00 (9H, s).

12B (3RS)-3-Benzyloxycarbonylamino-2,3-dihydro-5-(5-(1-((2-(trimethylsilyl)ethoxy) methyl))-imidazolyl)-1H-1,4-benzodiazepin-2-one The imidazole of example 12A (313 mg, 0.98 mmol) was converted to the benzodiazepine title compound by the method described in example 1C. The product was purified by chromatography (eluant 2% MeOH in EtOAc) to provide a yellow oil (204 mg, 41%).

¹H NMR (270 MHz, CDCl₃) δ 9.89 (1H, s); 8.58 (1H, d, J=8 Hz); 7.94–7.0 (10H, m); 6.67 (1H, d, J=8 Hz); 5.92 (1H, d, J=10.5 Hz); 5.59 (1H, d, J=10.5 Hz); 5.29 (1H, d, J=8 Hz); 5.17 (2H, s); 3.63 (2H, t, J=8 Hz); 0.93 (2H, t, J=8 Hz); 0.00 (9H, s) ppm.

12C (3RS)-3-Benzyloxycarbonylamino-1-((4-methylphenyl)carbonylmethyl)-2,3-dihydro-5-(5-(1-((2-trimethylsilyl)ethoxy)methyl))-imidazolyl)-1H-1,4-benzodiazepin-2-one The benzodiazepine of example 12C (60 mg, 0.118 mmol) was dissolved in DMF (5 ml) at 0° C. under N₂. Sodium hydride (15 mg, 80% disp. in oil) was added and the mixture stirred at r.t. 40 min. 2-Bromo-(4'-methyl)acetophenone (110 mg, 0.515 mmol) was then added and stirring continued at r.t. 2 h. The mixture was evaporated and partitioned between EtOAc and brine. The organic portion was filtered (Whatman 1PS phase separator) and evaporated and the product chromatographed on silica gel (eluant 90% EtOAc in hexanes→EtOAc) to provide the title compound as a pale yellow oil (35 mg, 48%).

$^1$H NMR (270 MHz, CDCl$_3$) δ 7.85–7.80 (3H, m); 7.63 (1H, d, J=7.5 Hz); 7.55 (1H, t, J=7.5 Hz); 7.37–7.23 (8H, m); 6.99 (1H, s); 6.63 (1H, d, J=8 Hz); 5.92 (1H, d, J=10 Hz); 5.61 (1H, d, J=10 Hz); 5.45 (1H, d, J=8 Hz); 5.37 (1H, d, J=17.5 Hz); 5.19–5.13 (3H, m); 3.63 (2H, m); 2.40 (3H, s); 0.93 (2H, m); 0.00 (9H, s) ppm.

12D N-((3RS)-1-(4-methylphenyl)carbonylmethyl-2,3-dihydro-2-oxo-5-(5-(1-((2-(trimethylsilyl)ethoxy)methyl))-imidazolyl)-1H-1,4-benzodiazepin-3-yl)-N'-(3-methylphenyl)urea The benzodiazepine of example 12C (35 mg, 0.055 mmol) was converted to the 3-methylphenyl urea as described in example 7G. The product was chromatographed on silica gel (eluant 95% EtOAc in hexanes) to provide a colourless oH (30 mg, 86%).

$^1$H NMR (270 MHz, CDCl$_3$) δ 7.88–7.73 (3H, m); 7.13 (1H, d, J=8 Hz); 7.58 (1H, t, J=8 Hz); 7.39–7.11 (7H, m); 6.97 (1H, d, J=7 Hz); 6.90 (1H, d, J=7 Hz); 6.68–6.57 (2H, m); 6.00 (1H, d, J=10 Hz); 5.72 (1H, d, J=7 Hz); 5.57 (1H, d, J=10 Hz); 5.34 (2H, s); 3.65 (2H, m); 2.47 (3H, s); 2.35 (3H, s); 0.92 (2H, m); 0.00 (9H, s) ppm.

12E N-((3RS)-1-(4-methylphenyl)carbonylmethyl-2,3-dihydro-2-oxo-5-(4-imidazolyl)-1H-1,4-benzodiazepin-3-yl)-N'-(3-methylphenyl)urea The benzodiazepine of example 12D (30 mg, 0.047 mmol) was treated with HBr gas as described in example 8B. The product was purified by MPLC on reverse-phase (C$_{18}$, eluting with a gradient of 20% MeCN in water to 100% MeCN) to provide a colourless solid when freeze dried (10 mg, 42%).

$^1$H NMR (270 MHz, CDCl$_3$) δ 7.70–6.40 (17H, m); 5.76 (1H, d, J=17 Hz); 5.64 (1H, d, J=8 Hz); 5.01 (1H, d, J=17 Hz); 2.26 (3H, s); 2.10 (3H, s) ppm.

EXAMPLE 13

N-((3RS)-1-tert-Butylcarbonylmethyl-2,3-dihydro-2-oxo-5-(3-pyrazolyl)-1H-1,4-benzodiazepin-3-yl)-N'-(3-methylphenyl)urea (Compound 9)

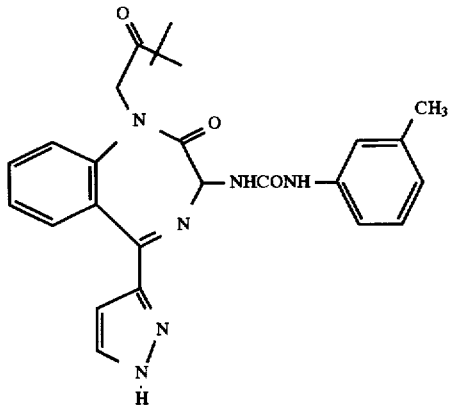

13A 3-(Hydroxy-(2-nitrophenyl))methyl pyrazole 1-(1-Pyrrolidino)methyl pyrazole (Katritsky et at., *J Org Chem* 1988, 53, 5685; 5.54 g, 36.7 mmol) was taken up in dry ether (120 ml) at −70° C. under N$_2$, and treated dropwise with n-butyl lithium (25.2 ml, 1.6M solution in hexanes). The mixture was stirred at −70° C. for 1½ h and then a solution of o-nitrobenzaldehyde (6.1 g, 40.4 mmol) added in dry THF (25 ml). The mixture was allowed to warm to r.t. over ½ h and then stirred for a further 2 h. 2M HCl (100 ml) was then added and stirring continued at r.t. 10 min. The two phases were separated and the aqueous portion neutralised with conc. ammonia and extracted with CHCl$_3$ (×2). The extracts were dried (MgSO$_4$), evaporated and chromatographed on silica gel (eluant 40% EtOAc in hexanes) to provide the title compound as a pale brown oil (2.51 g, 31%).

13B 3-(2-Nitrobenzoyl)-pyrazole

The pyrazole of example 13A (2.5g, 11.4 mmol) was oxidised with CrO$_3$ by the method described in example 7B. The product was crystallised from DCM-hexane to provide an off-white solid (1.78 g, 72%).

$^1$H NMR (270 MHz, CDCl$_3$) δ 13.5 (1H, br.s.); 8.18 (1H, d, J=8 Hz); 7.95–7.7 (4H, m); 6.94 (1H, s) ppm.

13C 3-(2-nitrobenzoyl)-1-((2-(trimethylsilyl)ethoxy)methyl)-pyrazole and 13D 5-(2-nitrobenzoyl)-1-((2-(trimethylsilyl)ethoxy)methyl)-pyrazole The pyrazole of example 13B (1.70 g, 7.835 mmol) was added in small portions to a stirring mixture of NaH (260 mg, 80% disp. in oil-hexane washed) in dry DMF (20 ml) at r.t. under nitrogen. The mixture was stirred at r.t. 2 h, then ((2-(trimethylsilyl)ethoxy) methyl)-chloride (1.5 g, 8.6 mmol) added dropwise. Stirring was continued for a further 2 h at r.t. and then the mixture poured into water (200 ml) and extracted with EtOAc (x 2). The extracts were filtered (Whatman 1PS phase separator), evaporated and chromatographed on silica gel (eluant 30% EtOAc in hexanes) to provide the two title compounds as a 1:1 mixture (2.35 g, 86%).

$^1$H NMR (270 MHz, CDCl$_3$) δ 8.24 (0.5H, d, J=8 Hz); 8.16 (0.5H, d, J=8 Hz); 7.8–7.5 (4H, m); 7.08 (0.5H, d, J=1 Hz); 6.33 (0.5H, d, J=1 Hz); 6.00 (1H, s); 5.39 (1H, s); 3.77 (1H, m); 3.46 (1H, m); 1.02 (1H, m); 0.92 (1H, m); 0.04 (4.5H, s); 0.00 (4.5H, s) ppm.

13E 3-(2-Aminobenzoyl)-1-((2-(trimethylsilyl)ethoxy)methyl)-pyrazole and 13F 5-(2-Aminobenzoyl)-1-((2-(trimethylsilyl)ethoxy)methyl)-pyrazole The mixture of pyrazoles of examples 13C and 13D (2.35 g, 6.772 mmol) was taken up in dry THF (100 ml) and degassed. 5% Pd.-on-carbon (1.2 g) was added and the mixture hydrogenated at 30 psi and ambient temperature for 2 h. The mixture was filtered (celite filter aid) and evaporated and then chromatographed (eluant 30% EtOAc in hexanes) to provide the two title compounds as an equimolar mixture (1.05 g, 49%).

$^1$H NMR (270 MHz, CDCl$_3$) δ 8.43 (0.5H, dd, J$_1$=8 Hz, J$_2$=1.5 Hz); 7.76–7.65 (1.5H, m); 7.39 (1H, m); 6.98 (0.5H, d, J=2.3 Hz); 6.81–6.63 (2.5H, m); 6.26 (2H, br.s.); 5.85 (1H, s); 5.60 (1H, s); 3.75–3.60 (2H, m); 1.02–0.90 (2H, m); 0.08 (4.5H, s); 0.00 (4.5H, s) ppm.

13G (3RS)-3-Benzyloxycarbonylamino-2,3-dihydro-5-(3-(1-((2-(trimethylsilyl)ethoxy) methyl))-pyrazolyl)-1H-1,4-benzodiazepin-2-one and 13H (3RS)-3-Benzyloxycarbonylamino-2,3-dihydro-5-(5-(1-((2-(trimethylsilyl)ethoxy) methyl))-pyrazolyl)-1H-1,4-benzodiazepin-2-one The mixture of pyrazoles, examples 13E and 13F, (1.0 g, 3.155 mmol) were converted to the benzodiazepine title compounds by the method described in example 1C. The product was purified by chromatography on silica gel (eluant 55% EtOAc in hexanes) to provide an equimolar mixture of the title compounds (1.21 g, 76%).

$^1$H NMR (270 MHz, CDCl$_3$) δ 8.64 (1H, m); 8.32 (1H, br.s.); 7.8–7.05 (9H, m); 6.96 (0.5H, d, J=1.4 Hz); 6.62 (1H, m); 6.41 (0.5H, br.s.); 5.96 (1H, s); 5.52–5.46 (1.54, m); 5.21 (2H, s); 5.09 (0.5H, br.s.); 3.56 (2H, m); 0.96 (2H, m); 0.09 (4.5H, s); 0.00 (4.5H, s) ppm.

13I (3RS)-Benzyloxycarbonylamino-1-tert-butylcarbonylmethyl-2,3-dihydro-5-(3-(1-((2-(trimethylsilyl)ethoxy)methyl))pyrazolyl)-1H-1,4-benzodiazepin-2-one and 13J (3RS)-Benzyloxycarbonylamino-1-tert-butylcarbonylmethyl-2,3-dihydro-5-(5-(1-((2-(trimethylsilyl)ethoxy)methyl))pyrazolyl)-1H-1,4-benzodiazepin-2-one The 1:1 mixture of benzodiazepines of examples 13G and 13H (1.10 g, 2.178 mmol) was alkylated with 1-bromopinacolone by the method described in. example 1D. The product was chromatographed (eluant 45% EtOAc in hexanes) to provide the title compounds as a equimolar mixture (860 mg, 66%).

$^1$H NMR (270 MHz, CDCl$_3$) δ 7.71 (1H, d, J=8 Hz); 7.6–7.0 (9H, m); 6.90 (1H, d, J=1.7 Hz); 6.67 (1H, d, J=8 Hz); 5.50 (1H, d, J=8 Hz); 5.43 (2H, m); 5.12 (2H, s); 5.02 (1H, d, J=17.5 Hz); 4.37 (1H, d, J=17.5 Hz); 3.59 (2H, m); 1.26 (9H, s); 0.94 (2H, m); 0.01 (4.51H, s); 0.00 (4.5H, s) ppm.

13K (3RS)-Amino-1-tert-butylcarbonylmethyl-2,3-dihydro-5-(3-pyrazolyl)-1H-1,4-benzodiazepin-2-one The mixture of benzodiazepines of examples 13I and 13J (350 mg, 0.58 mmol) was taken up in DCM (10 ml) and cooled to 0° C. Dry HBr gas was slowly bubbled through the mixture with stirring for 25 min. The mixture was then stoppered and stirred for a further 2 h at 0° C. The mixture was evaporated, taken up in 1M HCl and washed with ether. The aqueous portion was basified and extracted with CHCl$_3$ (x3). The combined extracts were washed with brine, filtered (Whatman 1PS phase separator) and evaporated. The residue was pure enough to be used in the next step without further purification (140 mg, 71%).

$^1$H NMR (270 MHz, CDCl$_3$) δ 7.67 (1H, dd, J$_1$=8 Hz, J$_2$=1.5 Hz); 7.60 (1H, d, J=2 Hz); 7.32–7.24 (2H, m); 7.09 (1H, d, J=8 Hz); 6.50 (1H, d, J=2 Hz); 5.09 (1H, d, J=17.5 Hz); 4.64 (1H, s); 4.41 (1H, d, J=17.5 Hz); 1.27 (9H, s) ppm.

13L N-((3RS)-1-tert-Butylcarbonylmethyl-2,3-dihydro-2-oxo-5-(3-pyrazolyl)-1H-1,4-benzodiazepin-3-yl-N'-(3-methylphenyl)urea The benzodiazepine of example 13K (70 mg, 0.2065 mmol) was taken up in DCM (2 ml) and m-tolyl isocyanate (32 μl) added. The mixture was stirred at r.t. 2 h, then evaporated and chromatographed on silica gel (eluant 80% EtOAc in hexanes) to provide the title compound which was freeze-dried from acetonitrile-water (22 mg, 23%).

$^1$H NMR (270 MHz, CDCl$_3$) δ 7.57·7.51 (3H, m); 7.35–7.02 (11H, m); 6.76 (1H, m); 6.38 (1H, d, J=2 Hz); 5.67 (1H, d, J=8 Hz); 4.8 (2H, m); 2.21 (3H, s); 1.19 (9H, s) ppm.

M.S. (+ve FAB) [M+H]$^+$=473.2

Compounds 10–16 of List A are obtainable by methods analogous to those described in the above examples.

EXAMPLE 14

Etoc-(1-benzotriazolyl)glycine

The title compound was prepared according to the method of Katritsky (J Org Chem 1990, 55, 2266). Ethyl carbamate (1.80 g, 20 mmol), glyoxylic acid hydrate (1.84 g, 20 mmol) and benzotriazole (2.38 g, 20 mmol) were heated under reflux together in benzene (60 ml) under Dean-Stark conditions for 2 h. The mixture was allowed to cool, diluted with ether (120 ml) and filtered to provide the tide compound as a colourless solid (3.73 g, 85%).

$^1$H NMR (270 MHz, CD$_3$OD) δ 7.6.5 (1H, d, J=8 Hz); 7.55 (1H, d, J=8 Hz); 7.22 (1H, t, J=8 Hz); 7.09 (1H, t, J=8 Hz); 6.83 (1H, s); 3.67 (2H, m); 0.84 (3H, m) ppm.

EXAMPLE 15

2-(2-Aminobenzoyl)pyridine

2-Bromopyridine-(13.11 g, 83.0 mmol) was dissolved in toluene (50 mL) under nitrogen. "BuLi (1.6M solution in "hexane; 50 mL, 80.0 mmol) was added dropwise to the solution below –60° C. After stirring was continued for a further 15 min at this temperature, a solution of anthranilonitrile (4.25 g, 35.0 mmol) in toluene (25 mL) was added dropwise to the solution over 8 min. below –60° C. After addition was complete, the mixture was stirred at –60° C. for 15 min. and then allowed to warm to 5° C. After stirring for an additional 2 h at 5° C., the mixture was poured into ice-cold 3N HCl (80 mL) and stirred at room temperature for 1 h. The separated organic portion was extracted with 1N HCl (40 mL). The combined aqueous portions were washed with toluene (20 mL) and basified to pH 9 with 25% aqueous ammonia at 0°–°5° C. Stirring was continued for a further 1 h at this temperature, and the resultant precipitate was collected by filtration, washed with water and dried to afford a crude solid (7.09 g). Recrystallisation from isopropanol provided crystalline product (I) (6.10 g, 86%).

EXAMPLE 16

(3RS)-(Ethoxycarbonyl)amino-2,3-dihydro-5-(2-pyridyl)-1H-1,4-benzodiazepin-2-one 2-(2-Aminobenzoyl)pyridine (1.39 g, 7 mmol) and Etoc-(1-benzotriazolyl) glycine (2.47 g, 11.2 mmol) were combined in DCM (25 nil) at 0° C. DMAP (100 mg) was added followed by water soluble carbodiimide (1.95 g, 10 mmol). The ice-bath was removed and stirring continued for 30 min. The mixture was evaporated and partitioned between EtOAc and 5% NaHCO$_3$. The organic portion was washed with brine, dried and evaporated. The product was taken up in ice-cold saturated ammonia in methanol (60 ml), stoppered and stirred at r.t. 1 h. The mixture was concentrated and taken up in acetic acid (80 ml) and stirred at r.t. 4 h. The mixture was concentrated and partitioned between CHCl$_3$ and 1M KOH. The organic portion was washed with brine, dried and concentrated and the product crystallised from EtOAc/hexane as a white solid (1.25 g, 55%).

$^1$H NMR (270 MHz, CHCl$_3$) δ 8.69 (1H, s); 8.62 (1H, d, J=1.5 Hz); 8.10 (1H, d, J=8 Hz); 7.83 (1H, dt, J$_1$=8 Hz, J$_2$=1.5 Hz); 7.50–7.17 (4H, m); 7.00 (1H, d, J=8.2 Hz); 5.36 (1H, d, J=8.2 Hz); 4.17 (2H, q, J=7 Hz); 1.29 (3H, t, J=7 Hz) ppm.

EXAMPLE 17

(3RS)-Ethyloxycarbonylamino-1-(tert-butylcarbonylmethyl)-2,3-dihydro-5-(2-pyridyl)-1H-1,4-benzodiazepin-2-one (3RS)-Ethyloxycarbonylamino-1,3-dihydro-5-(2-pyridyl)-2H-1,4-benzodiazepin-2-one (1.1 g, 3.395 mmol) was azeotroped with DMF then taken up in dry DMF (25 ml) at 0° C. under nitrogen. Sodium hydride (142 mg, 4.75 mmol) was added and the mixture allowed to warm to r.t. over 45 min. with stirring. 1-Bromopinacolone (760 mg, 4.25 mmol) was then added and stirring continued at r.t. for 45 min. The mixture was then quenched with water and evaporated. The residue was partitioned between CHCl$_3$ and brine and the organic portion dried and evaporated. The product was crystallised from EtOAc/hexane to provide an off-white solid (1.22 g, 85%).

$^1$H NMR (270 1 MHz, CDCl$_3$) δ 8.60 (1H, d, J=4 Hz); 8.15 (1H, d, J=8 Hz); 7.80 (1H, dt, J$_t$=8 Hz, J$_d$=1.6 Hz); 7.52 (1H, t, J=7 Hz); 7.40–7.20 (3H, m); 7.11 (1H, d, 8.2 Hz); 6.60 (1H, d, J=8.2 Hz); 5.49 (1H, d, J=8.2 Hz); 5.03 (1H, d, J=17.5 Hz); 4.48 (1H, d, J=17.5 Hz); 4.15 (2H, q, J=7 Hz); 1.29–1.24 (12H, m) ppm.

EXAMPLE 18

(3RS)-Amino-1-(tert-butylcarbonylmethyl)-2,3-dihydro-5-(2-pyridyl)-1H-1,4-benzodiazepin-2-one (3RS)-Ethyloxycarbonylamino-1-(tert-butylcarbonylmethyl)-2,3-dihydro-5-(2-pyridyl)-1H-1,4-benzodiazepin-2-one (IV, 250 mg, 0.592 mmol) was taken up in dry DCM (10 ml) at 0° C. and saturated with dry HBr gas. The mixture was stoppered and stirred at r.t. for 64 h. The solvent was evaporated and the product partitioned between 1M HCl and EtOAc. The acid portion was basified and extracted with CHCl$_3$ (×3). The extracts were combined and washed with brine, dried and evaporated to give a brown foam (188 mg, 91%), which was not purified further.

$^1$H NMR (CDCl$_3$, 270 MHz) δ 8.58 (1H, m); 8.08 (1H, d, J=8 Hz); 7.72 (1H, t, J=8 Hz); 7.41 (1H, t, J=8 Hz); 7.3–7.0 (5H, m); 5.00 (1H, d, J=17 Hz); 4.60 (1H, s); 4.38 (1H, d, J=17 Hz); 2.2 (2H, br.s); 1.22 (9H, s) ppm.

EXAMPLES 19 and 20

(3R) and (3S)-Amino-1-(tert-butylcarbonylmethyl)-2,3-dihydro-5-(2-pyridyl)-1H-1,4-benzodiazepin-2-one (3RS)-Amino-1-(tert-butylcarbonylmethyl)-2,3-dihydro-5-(2-pyridyl)-1H-1,4-benzodiazepine-2-one (2.2 g, 6.28 mmol) was taken up in MeCN (8 ml) at −5° C. (R)-mandelic acid (440 mg, 3.14 mmol) was added and the mixture stirred at −5° C. and seeded. As a thick precipitate began to form MeCN (8 ml) was added dropwise to enable easier filtration. After 1 hr at −5° C. the mixture was filtered and washed with small portions of cold MeCN. The resultant white precipitate (0.92 g, 30%) was recrystallised from MeCN. The salt was washed with base to give the free (R)-amine [α]$_D$=+212.6° (c=0.715, CHCl$_3$).

The filtrate from above was washed with base and taken up in MeCN (6 ml). Addition of (S)-mandelic acid afforded the (S)-amine salt in the same manner (0.85 g, 28%). This was recrystallised from MeCN and washed with base to provide the free (S)-amine [α]$_D$=−213.4° (c=0.671, CHCl$_3$).

The $^1$H NMR of each amine was identical to that for the (R,S)-mixture.

EXAMPLE 21

3-(Dimethylamino)phenyl isocyanate 3-(Dimethylamino)benzoic acid (350 g, 2.12 mol) was dissolved in acetone (2.8 L). Et$_3$N (249 g, 2.46 tool) was added dropwise to the solution below 10° C., followed by the addition of a solution of ethyl chloroformate (287 g, 2.65 mol) in acetone (875 mL) below 5° C. After stirring for 30 min, a solution of NaN$_3$ (201 g, 3.18 mol) in water (570 ml) was added dropwise below 5° C. The reaction mixture was stirred at 0°–5° C. for a further 1 h, then poured into toluene-ice water (2:3, 11 L). The aqueous portion was extracted with a small amount of toluene and the combined organic portions were washed with water and brine and dried (MgSO$_4$). After removing MgSO$_4$ by filtration, the filtrate was added dropwise to hot toluene (1.5 L). The mixture was refluxed for 1 h and then evaporated under reduced pressure. The residue was distilled (0.6–0.8 mmHg, 74°–77° C.) to afford the pure isocyanate (252 g, 74%) as a yellow oil.

EXAMPLE 22

N-((3R)-1-tert-Butylcarbonylmethyl-2,3-dihydro-2-oxo-5-(2-pyridyl)-1H-1,4-benzodiazepin-3-yl)-N'-((3-dimethylamino)phenyl)urea The (R)-amine of Example 19 (410 mg, 1.17 mmol) in DCM (5 ml) was treated with the isocyanate of Example 8 (1.05 equiv) and the mixture stirred at r.t. for 2 h, then evaporated. The title compound was obtained as a white solid by crystallisation from ethanol (550 mg, 91%).

[α]$_D$=+123.4 (c=0.316, CHCl$_3$).

$^1$H NMR (270 MHz, CDCl$_3$) δ 8.78 (1H, d, J=2 Hz); 8.27 (1H, d, J=8 Hz); 7.95 (1H, m); 7.65–6.6 (1 1H, m); 5.83 (1H, d, J=8 Hz); 5.05 (1H, d, J=16 Hz); 4.60 (1H, d, J=16 Hz); 3.0 (6H, s); 1.40 (9H, s) ppm.

Mass Spec (+FAB): [M+H]$^+$=513.4.

EXAMPLE 23

3-(Formylamino)benzoic acid

Acetic anhydride (76 ml) was added to 98% formic acid (130 ml) and the mixture stirred at r.t. 30 min, then 3-aminobenzoic acid (15 g, 109.5 mmol) added. The mixture was stirred at r.t. for 1 h, then water (1.3 L) added and stirring continued overnight. The resultant white precipitate was collected, washed with water and dried in vacuo over P$_2$O$_5$ (15.4 g, 85%).

EXAMPLE 24

N-Formyl-N-methylamino benzoic acid

3-Formylamino benzoic acid (2.28 g, 13.8 mmol) was taken up in DMF (25 ml) and added dropwise to a suspension of sodium hydride (1.05 g, 80% disp. in oil) in DMF (15 ml) at 0° C. The mixture was allowed to warm to r.t. over 1 h and then iodomethane (0.95 ml) added. A second portion of iodomethane (0.95 ml) was added after 1 h and the mixture stirred at r.t. overnight. The solvent was removed by evaporation and the product partitioned between ethyl acetate and 1M HCl. The organic layer was washed with brine, then filtered (Whatman® 1 PS phase separator) and evaporated. The residue was chromatographed on silica (eluant 60% ethyl acetate in hexanes) to provide the title compound as a colourless solid (2.30 g, 86%). A portion of the ester (900 mg, 4.66 mmol) was taken up in dioxan/water (2/1, v/v, 30 ml) and treated with LiOH.H$_2$O (378 mg, 9 mmol) at r.t. with stirring overnight. The mixture was acidified with 1M HCl and extracted twice with EtOAc. The combined extracts were washed with brine, filtered (Whatman® 1 PS phase separator) and evaporated. The acid (420 mg, 50%) was used in the next step without further purification.

EXAMPLE 25

N-((3RS)-1-tert-Butylcarbonylmethyl-2,3-dihydro-2-oxo-5-(2-pyridyl)-1H-1,4-benzodiazepin-3-yl)-N'-(3-(N-formyl-N-methylaminophenyl)urea The benzoic acid derivative of Example 11 (210 mg, 1.15 mmol) was suspended in toluene (25 ml) and treated with triethylamine (165 μl, 1.65 mmol) and diphenylphosphoryl azide (270 μl, 1.25 mmol) under nitrogen. The mixture was stirred at r.t. 1 h, then heated at reflux overnight. The mixture was cooled and evaporated and a solution of the me of Example 5 (250 mg, 0.71 mmol) added in DCM (8 ml). The resultant mixture was stirred at r.t. for 6 h, then evaporated and chromatographed on silica (eluant 80/20 EtOAc/hexane→neat EtOAc) to provide the title compound as a pale yellow solid (185 mg, 50%).

$^1$H NMR (270 MHz, CDCl$_3$) δ 8.62 (1H, d, J=2 Hz); 8.42 (1H, s); 8.01 (1H, d, J=8 Hz); 7.79 (1H, t, J=8 Hz); 7.15–6.70 (10H, m); 6.78 (1H, d, J=7 Hz); 5.76 (1H, d, J=7 Hz); 5.01 (1H, d, J=17 Hz); 4.63 (1H, d, J=17 Hz); 3.21 (3H, s); 1.36 (9H, s) ppm.

EXAMPLE 26

N-((3RS)-1-tert-Butylcarbonylmethyl-2,3-dihydro-2-oxo-5-(2-pyridyl)-1H-1,4-benzodiazepin-3-yl)-N'-(3-(methylamino)phenyl)urea The benzodiazepine of Example 25 (185 mg, 0.35 mmol) was taken up in acetone (5 ml) and treated with 4M HCl (3 ml). The mixture was stirred overnight at r.t., then evaporated and partitioned between DCM and 5% KHCO$_3$. The organic portion was filtered (Whatman® 1 PS phase separator), evaporated and chromatographed on silica (eluant 120/2/1, v/v/v, chloroform/methanol/acetic acid) to provide a colourless solid (67 mg, 88%).

$^1$H NMR (270 MHz, CDCl$_3$) δ 8.69 (1H, d, J=2 Hz); 8.24 (1H, d, J=8 Hz); 7.82 (1H, t, J=8 Hz); 7.59 (1H, t, J=8 Hz); 7.46–7.0 (9H, m); 6.80 (1H, br.s); 6.58 (1H, d, J=8 Hz); 6.37 (1H, d, J=8 Hz); 5.80 (1H, d, J=8 Hz); 4.99 (1H, d, J=17 Hz); 4.58 (1H, d, J=17 Hz); 2.82 (3H, s); 1.30 (9H, s) ppm.

Mass Spec (+ve FAB): [M+H]$^+$=499.3.

EXAMPLE 27

3-(tert-Butyloxycarbonylamino)benzoic acid

3-Aminobenzoic acid (4.11 g, 30 mmol) was taken up in 2M KOH (30 ml) and dioxan (30 ml). The solution was cooled to 0° C. and di-tert-butyldicarbonate (6.98 g, 32 mmol) added. The mixture was allowed to warm to r.t. and stirred overnight. Dioxan was removed by evaporation and the solution diluted with 1H KOH (50 ml). The mixture was washed with ether (×2) and acidified with conc. HCl. The resultant white precipitate was collected by filtration and dried over P$_2$O$_5$ (5.35 g, 75%).

EXAMPLE 28

N-((3R)-1-tert-Butylcarbonylmethyl-2,3-dihydro-2-oxo-5-(2-pryridyl)-1H-1,4-benzodiazepin-3-yl)-N'-(3-aminophenyl)urea The benzoic acid derivative of Example 27 (1.19 g, 5 mmol) was taken up in benzene (20 ml) and triethylamine (1.2 ml) and treated with diphenylphosphoryl azide (2.25 g). The mixture was heated at 80° C. overnight then cooled and evaporated. The chiral amine of Example 6 (850 mg, 2.43 mmol) was added in CHCl$_3$ (10 ml) and the mixture stirred at r.t. for 3 h. The mixture was evaporated and chromatographed on silica (eluant 70% EtOAc in hexanes→EtOAc) to provide a colourless oil (1.4 g). This residue was taken up in DCM (10 ml) and treated with TFA (30 ml) at r.t. for 45 min under nitrogen. The mixture was evaporated and partitioned between EtOAc and 5% KHCO$_3$. The organic portion was filtered (Whatman 1 PS, phase separator), evaporated and chromatographed (eluant 6% MeOH in CHCl$_3$) to provide a hygroscopic colourless solid (788 mg, 67%).

$^1$H NMR (270 MHz, CDCl$_3$) δ 8.59 (1H, d, J=2 Hz); 8.08 (1H, d, J=8 Hz); 7.62 (1H, t, J=8 Hz); 7.44 (1H, t, J=8 Hz); 7.4–6.8 (12H, m); 5.68 (1H, d, J=8 Hz); 4.80 (1H, d, J=16 Hz); 4.60 (1H, d, J=16 Hz); 1.40 (9H, s) ppm.

Mass Spec (+ve FAB): [M+H]$^+$=485.3.

EXAMPLE 29

3-Phenacyl pyridazine

3-Phenacyl pyridazine was prepared in 53% yield according to the method outlined in Example 5A.

EXAMPLE 30

3-((2-Benzoylamino)benzoyl)pyridazine

The ketone of Example 29 (5.5 g, 27.8 mmol) and fleshly distilled phenyl hydrazine (2.75 ml, 27.8 mmol) were stirred together in refluxing toluene under Dean-Stark conditions for 4 h. Zinc chloride (2.5 g) was added and reflux continued overnight. The stirring mixture was allowed to cool to r.t. and the resultant precipitate filtered to provide the crude indole as a mixture with zinc salts (9.25 g). The crude product (3 g) was taken up in acetic acid (80 ml), CrO$_3$ (4.8 g) added and the mixture stirred at 70° C. for 3 h, then cooled, basified with 3M KOH and extracted with EtOAc. The combined extracts were dried (MgSO$_4$) and chromatographed on silica (eluant 80% EtOAc in hexanes) to provide a yellow solid (1.46 g, 44%, two steps).

$^1$H NMR of crude indole (270 MHz, d$_6$ DMSO) δ 11.90 (1H, br.s); 9.07 (1H, dt, J$_d$=8 Hz, J$_t$=1.5 Hz); 7.95 (1H, d, J=8 Hz); 7.6–7.3 (8H, m); 7.23 (1H, t, J=8 Hz); 7.14 (1H, t, J=8 Hz) ppm.

$^1$H NMR of 3-(2-Aminobenzoyl) pyridazine (270 MHz, CDCl$_3$) δ 12.16 (1H, br.s); 9.34 (1H, dd, J$_1$=5 Hz, J$_2$=1.5 Hz); 8.97 (1H, d, J=8 Hz); 8.10–7.40 (9H, m); 7.15 (1H, t, J=8 Hz) ppm.

EXAMPLE 31

3-(2-Aminobenzoyl)pyridazine

The benzamide of Example 30 (700 mg, 2.31 mmol) was taken up in ethanol (8 ml) and treated with 5M KOH (20 ml) at 80° C. for 4 h. The mixture was cooled, diluted with 5% KHCO$_3$ and extracted with EtOAc. The extracts were filtered (Whatman® 1 PS, phase separator) and evaporated and the residue chromatographed (eluant 70% EtOAc in hexanes) to provide the title compound as a yellow crystalline solid (160 mg, 32%).

$^1$H NMR (270 MHz, CDCl$_3$) δ 9.30 (1H, dd, J$_1$=5 Hz, J$_2$=1.5 Hz); 7.90 (1H, dd, J$_1$=7.5 Hz, J$_2$=1.5 Hz); 7.75 (1H, d, J=7.5 Hz); 7.68 (1H, m); 7.33 (1H, m); 6.73 (1H, d, J=9 Hz); 6.62 (1H, t, J=7.5 Hz); 6.40 (2H, br.s) ppm.

EXAMPLE 32

(3RS)-Benzyloxycarbonylamino-2,3-dihydro-2-oxo-5-(3-pyridazinyl)-1H-1,4-benzodiazepin-2-one The title compound was prepared from the amino ketone of Example 31 (160 mg, 0.805 mmol) as described in Example 1C. The product was purified by crystallisation from EtOAc/ether/hexane to provide a pale yellow solid (91 mg, 30%).

$^1$H NMR (270 MHz, CDCl$_3$) δ 9.25 (1H, dd, J$_1$=5 Hz, J$_2$=1.5 Hz); 8.34 (1H, d, J=8 Hz); 8.19 (1H, br.s); 7.63–7.24

(9H, m); 7.12 (1H, d, J=8 Hz); 6.69 (1H, d, J=8 Hz); 5.47 (1H, d, J=8 Hz); 5.17 (2H, s) ppm.

EXAMPLE 33

(3RS)-Benzyloxycarbonylamino-1-tert-butylcarbonylmethyl-2,3-dihydro-5-(3-pyridazinyl)-1H-1,4-benzodiazepin-2-one The benzodiazepine of Example 32 (85 mg, 0.2196 mmol) was alkylated with 1-bromopinacolone as described in Example 1D. The product was chromatographed on silica (eluant EtOAc) to provide a yellow solid (75 mg, 70%).

$^1$H NMR (270 MHz, CDCl$_3$) δ 9.23 (1H, dt, J$_f$=5 Hz, J$_d$=1.5 Hz); 8.37 (1H, d, J=9.5 Hz); 7.62–7.50 (3H, m); 7.37–7.23 (6H, m); 7.13 (1H, d, J=8 Hz); 6.75 (1H, d, J=8 Hz); 5.57 (1H, d, J=8 Hz); 5.14 (2H, s); 5.01 (1H, d, J=17.8 Hz); 4.46 (1H, d, J=17.8 Hz); 1.25 (9H, s) ppm.

EXAMPLE 34

N-((3RS)-1-tert-Butylcarbonylmethyl-2,3-dihydro-2-oxo-5-(3-pyridazinyl)-1H-1,4-benzodiazepin-3-yl)-N'-(3-dimethylaminophenyl)urea The title compound was prepared from the benzodiazepine of Example 33 (70 mg, 0.144 mmol) by the method described in Examples 5F and 6. The product was purified by chromatography (eluant 3% MeOH in EtOAc) and the resultant solid crystallised from MeCN/ether (12 mg, 17%).

$^1$H NMR (270 MHz, CDCl$_3$) δ 9.19 (1H, d, J=5 Hz); 8.33 (1H, d, J=8.5 Hz); 7.6–7.48 (2H, m); 7.30–7.00 (6H, m); 7.90 (1H, br.s); 6.60–6.44 (2H, m); 5.77 (1H, d, J=8 Hz); 4.95 (1H, d, J=18 Hz); 4.53 (1H, d, J=18 Hz); 2.91 (6H, s); 1.22 (9H, s) ppm.

Mass Spec (+ve FAB): [M+H]$^+$=514.5.

EXAMPLE 35

Methyl 3-(4-pentenoylamino)benzoate

Methyl(3-amino)benzoate (4.5 g, 29.8 mmol) was taken up in DCM (10 ml) and pyridine (1 ml) at 0° C. 4-Pentenoyl chloride (freshly prepared from 4-pentenoic acid (3.0 g, 29.97 mmol) and thionyl chloride (6.6 ml) at r.t. for 1 h, evaporated and azeotroped with DCM) was added dropwise in DCM (3 ml). The mixture was allowed to warm to r.t. and stirred overnight. The mixture was evaporated and partitioned between EtOAc and 1M HCl. The organic portion was washed with 5% KHCO$_3$ and brine, filtered (Whatman® 1PS, phase separator), and evaporated. The residue was chromatographed (eluant 30% EtOAc in hexanes) to provide a colourless oil (2.20 g, 32%).

$^1$H NMR (270 MHz, CDCl$_3$) δ 8.05 (1H, t, J=1.5 Hz); 7.93 (1H, d, J=8 Hz); 7.79 (1H, d, J=8 Hz); 7.56 (1H, br.s); 7.42 (1H, t, J=8 Hz); 5.92 (1H, m); 5.2–5.0 (2H, m); 3.93 (3H, s); 2.51 (4H, m) ppm.

EXAMPLE 36

Methyl 3-(5-bromopentanoylamino)benzoate

The compound of Example 35 (1.7 g, 7.3 mmol) was taken up in dry THf (25 ml) at r.t. under nitrogen. 9-BBN (20 ml, 0.5M solution) was added and the mixture stirred at r.t. for 3 h. 1M NaOH (8 ml) was then added followed by 27% hydrogen peroxide (2.5 ml, dropwise). Stirring was continued at 40° C. for 1 h, then the mixture evaporated, taken up in EtOAc and washed with 5% KHCO$_3$ and brine. The organic portion was filtered (Whatman® 1 PS, phase separator), evaporated and chromatographed (eluant 95% EtOAc in hexanes) to provide the alcohol as a mixture with borates. The product was taken up in DCM (120 ml) and treated with triphenyl phosphine (5 g) and carbon tetrabromide (6.2 g) at r.t. for 2 h with stirring. The mixture was then evaporated and chromatographed (eluant 40% EtOAc in hexanes) to provide a colourless oil which crystallised on standing (1.54 g, 67%).

$^1$H NMR (270 MHz, CDCl$_3$) δ 9.62 (1H, br.s); 8.26 (1H, t, J=1.5 Hz); 7.95–7.8 (2H, m); 7.4 (1H, m); 3.96 (3H, s); 3.44 (2H, m); 2.66 (2H, m); 1.98 (4H, m) ppm.

EXAMPLE 37

Methyl 3-(2-oxo-1-piperidinyl)benzoate

The bromide of Example 36 (1.50 g, 4.88 mmol) was taken up in dry DMF (40 ml) and treated with NaH (160 mg, 80% disp. in oil) at 0° C. The mixture was stirred at r.t. under nitrogen for 10 min, then KI (80 mg) added and the mixture heated at 70° C. for 4 h. The mixture was evaporated and partitioned between EtOAc and 1M HCl. The organic portion was washed with 5% KHCO$_3$ and brine, filtered (Whatman® 1 PS, phase separator) and evaporated. The residue was chromatographed (eluant 2% MeOH in EtOAc) to provide a colourless oil (640 mg, 56%).

$^1$H NMR (270 MHz, CDCl$_3$) δ 8.1–7.95 (2H, m); 7.60–7.50 (2H, m); 3.98 (3H, s); 3.75 (2H, m); 2.64 (2H, m); 2.03 (4H, m) ppm.

EXAMPLE 38

Methyl 3-(1-piperidinyl)benzoate

The compound of Example 37 (640 mg, 2.75 mmol) was dissolved in dry THF (30 ml) and borane-tetrahydrofuran complex (5 ml, 1M solution in THF) was added. The mixture was stirred under nitrogen under reflux for 1 h, then cooled and evaporated. The residue was taken up in MeOH/acetic acid (6/1, v/v, 70 ml) and heated under reflux for 3 h, then evaporated and chromatographed (eluant 10% EtOAc in hexanes) to provide a colourless oil (540 mg, 90%).

$^1$H NMR (270 MHz, CDCl$_3$) δ 7.59 (1H, t, J=1.5 Hz); 7.46 (1H, dd, J$_1$=8 Hz, J$_2$=1.5 Hz); 7.28 (1H, t, J=8 Hz); 7.11 (1H, m); 3.89 (3H, s); 3.18 (2H, m); 1.75–1.62 (4H, m); 1.61–1.55 (2H, m) ppm.

EXAMPLE 39

3-(1-Piperidinyl)benzoic acid

The compound of Example 38 (540 mg, 2.466 mmol) was dissolved in dioxan (12 ml) and water (8 ml). Lithium hydroxide hydrate (300 mg, 7.143 mmol) was added and the mixture stirred at 40° C. for 1 h. The mixture was acidified with acetic acid, evaporated, azeotroped with toluene and chromatographed on silica (eluant 60/40/2, v/v/v, EtOAc/hexanes/AcOH) to provide a colourless solid (450 mg, 90%).

$^1$H NMR (270 MHz, CDCl$_3$) δ 7.66 (1H, s); 7.54 (1H, d, J=8 Hz); 7.32 (1H, t, J=8 Hz); 7.17 (1H, dd, J$_1$=8 Hz, J$_2$=1.5 Hz); 3.22 (4H, m); 1.72 (4H, m); 1.61 (2H, m) ppm.

EXAMPLE 40

N-((3R)-1-tert-Butylcarbonylmethyl-2,3-dihydro-2-oxo-5-(2-pyridyl)-1H-1,4-benzodiazepin-3-yl)-N'-(3-(1-piperidinyl)phenyl)urea 3-(1-Piperidyl)benzoic acid (225 mg, 1.097 mmol) was converted to the isocyanate using the method described in Example 2. To a solution of the isocyanate in DCM (5 ml) was added the benzodiazepine of Example 19 (220 mg, 0.6286 mmol). The mixture was stirred at r.t. for 1 h, then evaporated and chromatographed (eluant 90% EtOAc in hexanes) to provide a white solid which was recrystallised from MeCN (180 mg, 52%).

$[\alpha]_D$=+117° (c=0.296, CHCl$_3$).

$^1$H NMR (270 MHz, CDCl$_3$) δ 8.59 (1H, d, J=6 Hz); 8.15 (1H, d, J=8 Hz); 7.75 (1H, t, J=6 Hz); 7.50 (1H, t, J=6 Hz); 7.4–6.9 (8H, m); 6.61 (2H, m); 5.73 (1H, d, J=8 Hz); 4.96 (1H, d, J=17.5 Hz); 4.50 (1H, d, J=17.5 Hz); 3.12 (4H, m); 1.73–1.52 (6H, m); 1.22 (9H, s) ppm.

Mass Spec (+ve FAB) [M+H]$^+$=553.4.

EXAMPLE 41

(3RS)-tert-Butyloxycarbonylamino-2,3-dihydro-2-oxo-5-phenyl-1H-1,4-benzodiazepin-2-one tert-Butylcarbamate (15 g), benzotriazole (15.26 g) and glyoxilic acid hydrate (11.8 g) were mixed together in benzene (250 ml) and heated under reflux with the aid of a Dean-Stark separator as described (Katritsky, *J Org Chem* 1990, 55, 2266).

The mixture was cooled and extracted twice with 5% NaHCO$_3$ and the combined aqueous extracts washed with ether then acidified and extracted with EtOAc. The EtOAc extracts were washed with brine, dried (MgSO$_4$) and evaporated. The residue was (taken up in DCM (80 ml) and treated with DMAP (0.4 g) and 2-aminobenzophenone (8 g, 40.4 mmol). The mixture was cooled to 0° C. with stirring and water soluble carbodiimide (10 g) added. Stirring was continued at r.t. for 3 h, after which time the mixture was evaporated and partitioned between EtOAc and 5% KHCO$_3$. The organic portion was washed with 1M HCl and brine, dried and filtered (Whatman® 1 PS phase separator) then evaporated to dryness. The residue was taken up in an ice-cold saturated solution of ammonia in methanol, stoppered and stirred at r.t. for 45 min. The mixture was re-cooled and evaporated. The residue was suspended in ether 100 ml and 1M HCl (250 ml). The ether was decanted and the aqueous portion basified and extracted with EtOAc (×2). The combined extracts were washed with brine, dried (MgSO$_4$) and evaporated. The resultant solid was recrystallised from EtOAc/hexanes to provide a white solid (8.62 g, 61%).

$^1$H NMR (270 MHz, CDCl$_3$) δ 8.41 (1H, br.s); 7.60–7.14 (9H, m); 6.36 (1H, d, J=8.8 Hz); 5.32 (1H, d, J=8.8 Hz); 1.48 (9H, s).

EXAMPLE 42

N-((3R)-1-tert-Butylcarbonylmethyl-2,3-dihydro-2-oxo-5-2-pyridyl)-1H-1,4 -benzodiazepin-3-yl)-N'-(3-methylphenyl)urea The chiral (R)-amine of Example 19 (750 mg, 2.14 mmol) was taken up in dry DCM (10 ml) at 0° C. and treated with m-tolylisocyanate (0.33 ml, 2.57 mmol). The mixture was stirred at r.t. for 2 h, then evaporated and chromatographed on silica (eluant 70% EtOAc in hexanes). The residue was recrystallised from EtOAc/hexane to provide a white crystalline solid (955 mg, 92%).

Mass Spec (+ve FAB): [M+H]$^+$=484.2.

$^1$H NMR (270 MHz, CDCl$_3$) δ 8.79 (1H, d, J=3 Hz); 8.30 (1H, d, J=8 Hz); 7.96 (1H, t, J=8 Hz); 7.63 (1H, t, J=8 Hz); 7.55–6.95 (10H, m); 5.83 (1H, d, J=8 Hz); 5.08 (1H, d, J=17 Hz); 4.71 (1H, d, J=17 Hz); 2.41 (3H, s); 1.38 (9H, s) ppm.

$[\alpha]_D$=+119.8° (c=0.272, CHCl$_3$).

EXAMPLE 43

Ethoxycarbonyl-(1-benzotriazolyl)glycine (Alternative procedure to Example 14)

Ethyl carbamate (69.0 g, 774.5 mmol), glyoxylic acid hydrate (71.3 g, 774.5 mmol) and benzotriazole (92.0 g, 774.5 mmol) were dissolved in toluene (2.3 l) and the mixture was heated with distillation for 3 h to precipitate the product. The mixture was diluted with toluene (totally 2.3 l) and stirred at 15° C. overnight. The resultant precipitate was collected by filtration, washed with toluene (160 ml) and dried to afford the title compound (196.06 g, 96%): mp. 189°–192° C.

EXAMPLE 44

2-(2-Aminobenzoyl)pyridine (Alternative procedure to Example 15)

2-Aminobenzonitrile (58.3 g, 493.6 mmol), and 2-bromopyridine (132.5 g, 838.6 mmol) were dissolved in toluene (875 ml) and the mixture was cooled below –30° C. under nitrogen. $^n$BuLi (15% solution in $^n$hexane; 700 ml, 1.09 mol) was added dropwise to the mixture below –30° C. The mixture was allowed to warm to 0° C. and stirring was continued for 1.5 h. The mixture was poured into 3M HCl (800 ml) below 15° C. and stirred for 15 min. The separated organic portion was extracted with 3M HCl (200 ml). The combined aqueous portions were washed with toluene (200 ml), basified to pH 9 with 25% NaOH below 5° C. and stirred at r.t. overnight. The resultant precipitate was collected by filtration, which was recrystallised from isopropanol (880 ml) to afford the title compound (70.05 g, 72%): mp. 145°–146° C.

EXAMPLE 45

(3RS)-Ethoxycarbonylamino-2,3-dihydro-5-(2-pyridyl)-1H-1,4-benzodiazepin-2-one (Alternative procedure to Example 16, using DCC instead of WSC and DMAP.)

2-(2-Aminobenzoyl)pyridine (56.4 g, 284.5 mmol) and EtOC-(1-benzotriazolyl)glycine (94.1 g, 356.1 mmol) were combined in DCM (850 ml). A solution of DOC (83.8 g, 406.1 mmol) in DCM (80 ml) was added dropwise at 0°–5° C. and the mixture was stirred for 1 h. 5% NaHCO$_3$ (1 l) was added to the mixture and stirring was continued for 1 h. The resultant precipitate was filtered off and the organic portion was washed with brine (600 ml) and concentrated to ca. 300 ml. The mixture was diluted with methanol (500 ml) and concentrated to ca. 500 ml.

20% ammonia in methanol (600 ml) was added to the solution below 5° C. and the mixture was stirred below 10° C. for 3 h. Acetic acid (500 ml) was added to the solution below 15° C., and the mixture was stirred at 0° C. overnight and evaporated. CHCl$_3$ (1.5 l) and water (500 ml) were added to the residue and basified to pH 9 with 25% NaOH. The organic portion was washed with brine (700 ml) and concentrated to ca. 500 ml. The mixture was diluted with EtOAc (1.5 l), concentrated to ca. 1.5 l at atmospheric pressure and stirred at 0° C. overnight. The resultant precipitate was collected by filtration to afford the title compound (70.55 g, 77%): mp. 220°–223° C.

EXAMPLE 46

(3RS)-Ethoxycarbonylamine-1-(tert-butylcarbonylmethyl)-2,3-dihydro-5-(2-pyridyl)-1H-1,4-benzodiazepin-2-one (Minor changes to Example 17)

(3RS)-Ethoxycarbonylamino-2,3-dihydro-5-(2-pyridyl)-1H-1,4-benzodiazepin-2-one (14.6 g, 45.0 mmol) was taken up in dry DMF (73 ml). Sodium hydride (1.4 g, 58.5 mmol) was added portionwise below 5° C. and the mixture was stirred at r.t. for 1 h. 1-Bromopinacolone (10.21 g, 57.0 mmol) was then added dropwise below 10° C. and stirring was continued at r.t for 1 h. The mixture was evaporated, taken up in DCM (73 ml) and washed with 5% NaHCO$_3$ and brine. The organic portion was evaporated and recrystallised from EtOAc/hexane (1:1, v/v, 146 ml) to provide the title compound as a white solid (15.4 g, 81%): top. 214°–216° C.

EXAMPLE 47

(3RS)-Amino-1-(tert-butylcarbonylmethyl)-2,3-dihydro-5-(2-pyridyl)-1H-1,4-benzodiazepin-2-one (Alternative to Example 18, using TMS-I instead of HBr to give higher yield with clean reaction)

Hexamethyldisilane (4.36 g, 29.8 mmol) was added dropwise to the suspension of iodine (7.51 g, 29.6 mmol) in DCM (27 ml) at 30°–35° C. and the mixture was stirred at 30° C. for 1 h.

A solution of (3RS)-ethoxycarbonylamino-1-(tert-butylcarbonylmethyl)-2,3-dihydro-5-(2-pyridyl)-1H-1,4-benzodiazepin-2-one (10.0 g, 23.7 mmol) in DCM (40 ml) was added to the above solution below 25° C. and the mixture was stirred for 50 h. The mixture was then poured into 3M HCl (80 ml) below 25° C. and the aqueous portion was washed with DCM (10 ml×2). The combined organic portions were extracted with 3M HCl (20 ml). DCM (50 ml) was added to the combined aqueous portions and the mixture was basified to pH 10 with 25% NaOH below 5° C. The organic portion was washed with brine (50 ml) and evaporated. CH$_3$CN (50 ml) was added and the mixture was filtered to remove the small amount of insoluble material. The filtrate was evaporated to give the title compound as a brown foam (7.75 g, 93%), which was not purified further.

Example 48

3-tert-Butoxycarbonylaminobenzoic acid (Minor changes to Example 27)

3-Aminobenzoic acid (24.69 g, 180.0 mmol) was taken up in 2M KOH (180 ml) and dioxane (180 ml), and treated with di-tert-butyl dicarbonate (53.03 g, 245.0 mmol) at r.t. overnight. Dioxane was removed by evaporation and the solution was diluted with 1M KOH (300 ml). The aqueous portion was washed with ether (200 and 300 ml) and acidified to pH 4 with conc. HCl. The resultant white precipitate was collected by filtration, washed with water and dried in vacuo (P$_2$O$_5$) to give the title compound (38.97 g, 91%).

EXAMPLE 49

N-((3R)-1-tert-Butylcarbonylmethyl-2,3-dihydro-2-oxo-5-(2-pyridyl)-1H-1,4-benzodiazepin-3-yl)-N'-(3-dimethylaminophenyl)urea hydrochloride N-((3R)-1-tert-Butylcarbonylmethyl-2,3-dihydro-2-oxo-5-(2-pyridyl)-1H-1,4-benzodiazepin-3-yl)-N'-(3-dimethylaminophenyl)urea (70 g, 136.6 mmol) was taken up in ethanol (1 l) and 2.26M HCl ethanol (63.5 ml, 143.4 mmol) was added dropwise. The mixture was warmed up to 50° C. to afford a clear solution, which was seeded, cooled to 0° C. and stirred at the same temperature overnight. The resultant precipitate was collected by flirtation to provide the title compound as a white crystalline (62.4 g, 82%): top. 181°–184° C.

$^1$H NMR (400 MHz, DMSO-d$_6$) δ 9.46 (1H, br.s); 8.61 (1H, d, J=5 Hz); 8.02 (2H, m); 7.66 (3H, m); 7.57 (1H, t, J=6 Hz); 7.45 (1H, d, J=8 Hz); 7.34 (3H, m); 7.20 (1H, br.s); 7.07 (1H, br.s); 5.41 (1H, d, J=8 Hz); 5.05 (1H, d, J=18 Hz); 4.85 (1H, d, J=18 Hz); 3.02 (6H, s); 1.17 (9H, s) ppm.

EXAMPLE 50

3-(N-tert-Butoxylcarbonyl-N-methylamino)benzoic acid

Sodium hydride (18.33 g, 60% disp. in oil, 458.3 mmol) was added portionwise to a solution of 3-tert-butoxycarbonylaminobenzoic acid (43.48 g, 183.3 mmol) in DMF (600 ml) below 10° C. and the mixture was allowed to warm to r.t. with stirring over 1 h. MeI (84.54 g, 595.6 mmol) was added dropwise to the solution for 30 min at 5° C. and the mixture was stirred at r.t. for 2 h. The mixture was evaporated and the residue was partitioned between EtOAc (1.2 l) and water (600 ml). The organic portion was washed with sat. NaHCO$_3$ (100 ml) and water (200 ml×5), dried (MgSO$_4$) and evaporated.

The residual oil was taken up in methanol (1 l), 1M LiOH (185 ml) was added to the solution at 5° C. and the mixture was stirred at r.t. for 12 h. A further 1M LiOH (90 ml) was added to the mixture and stirred for 1 h. The solution was evaporated to remove methanol, diluted with water and washed with EtOAc/hexane (1:2, v/v, 300 and 150 ml). The aqueous portion was acidified to pH 4 with conc. HCl and extracted with EtOAc (400 and 200 ml). The combined organic portions were washed with brine, dried (MgSO$_4$) and evaporated. The residue was recrystallised from EtOAc/hexane (1:20, v/v, 420 ml) to give the title compound (36.08 g, 78%).

EXAMPLE 51

3-(N-tert-Butoxylcarbonyl-N-methylamino)phenyl isocyanate

Et$_3$N (3.71 g, 36.7 mmol) and a solution of ethyl chloroformate (4.31 g, 39.7 mmol) in acetone (10 ml) were successively added dropwise to a solution of 3-(N-tert-butoxylcarbonyl-N-methylamino)benzoic acid (8.0 g, 31.8 mmol) in acetone (64 ml) below 5° C. After stirring for 30 min, a solution of NaN$_3$ (3.10 g, 47.7 mmol) in water (10 ml) was added to the solution below 5° C. The mixture was stirred at the same temperature for a further 1 h, then poured into toluene (80 ml) and water (160 ml). The organic portion was washed with brine, refluxed for 2 h and evaporated. The residue was distilled (100°–105° C./0.9–1.0 mmHg) to afford the title compound (6.2 g, 78%) as a yellow oil.

EXAMPLE 52

N(-((3R)-1-tert-Butylcarbonylmethyl-2,3-dihydro-2-oxo-5-(2-pyridyl)-1H-1,4-benzodiazepin-3-yl)-N'-3-methylaminophenyl)urea 3-(N-tert-Butoxylcarbonyl-N-methylamino)phenyl isocyanate (19.30 g, 77.7 mmol) was added dropwise to a solution of the chiral-amine of Example 19 (27.19 g, 77.6 mmol) in DCM (200 ml) below 20° C. and the mixture was stirred at r.t. for 30 min, then evaporated. The residue was taken up in EtOAc (200 ml) and water (100 ml), conc. HCl (120 ml) was added dropwise to the mixture below 20° C. and stirred for 3 h. DCM (500 ml) was added to the separated aqueous portion and basified to pH 10 with 20% NaOH below 20° C. The organic portion was washed with brine (300 ml), evaporated and crystallised from ethanol. The resultant precipitate was collected by flirtation and recrystallised from ethanol (1.8 l) to provide the title compound as a white crystalline (27.30 g, 72%): mp. 243°–246° C.

$^1$H NMR (400 MHz, CDCl$_3$) δ 8.60 (1H, d, J=5 Hz); 8.15 (1H, d, J=8 Hz); 7.77 (1H, dt, J$_f$=8 Hz, J$_d$=1.5 Hz) 7.51 (1H, dt, J$_r$=8 H, J$_d$=1.5 Hz) 7.39–6.76 (9H, m); 6.54 (1H, d, J=8Hz); 6.30 (1H, dd, J=8, 1.5 Hz); 5.72 (1H, d, J=8 Hz); 4.96 (1H, d, J=18 Hz); 4.54 (1H, d, J=18 Hz); 2.78 (3H, s); 1.23 (9H, s) ppm.

Mass Spec (+ve FAB): [M+H]$^+$=499.

The compounds of and prepared by the present invention are potent and selective antagonists at the CCK-B receptor and inhibit gastric acid secretion stimulated by pentagastrin. Methods of measuring these activities are described below.

Measurement of binding affinity for CCK-B receptors

About 100 SD rats were decapitated without anaesthesia, the whole brain was immediately excised from each of the rats and homogenized in 10-fold volume of 0.32M aqueous solution of sucrose by the use of a Teflon-coated homogenizer, the homogenate thus obtained was centrifuged for ten minutes at 900 G by the use of a cooled centrifuge, and the supernatant was further centrifuged for 15 minutes at 11500 G. The precipitate thus obtained was dispersed in 50 mM Tris-HCl buffer (pH 7.4) containing 0.08% Triton X-100, this suspension was allowed to stand for 30 minutes and again centrifuged for 15 minutes at 11500 G, the precipitate thus obtained was washed twice with 5 mM Tris-HCl buffer and twice with 50 mM Tris-HCl buffer in that order with centrifugal separation, the washed precipitate was suspended in 50 mM Tris-HCl buffer, and the suspension thus obtained was stored at –80° C. until the membrane preparation was required.

The membrane preparations were warmed to room temperature, diluted with 10 mM HEPES buffer (containing 130 mM NaCl, 5 mM MgCl$_2$, 1 mM EGTA and 0.25 mg/ml bacitracin; pH 6.5) and incubated at 25° C. for 120 minutes in the presence of [$^{125}$I]BH-CCK-8 and the test compound, then separated by suction filtration. Non-specific binding was determined in the presence of 1 μM CCK-8. The amount of labelled ligand bound to the receptor was measured by the use of a γ-counter, IC$_{50}$ values were determined, being that concentration of test compound required to inhibit specific binding by 50%.

IC$_{50}$ values for the compounds of this invention were in the range 0.1 to <100 nM; representative examples are shown below.

| | IC$_{50}$ (nM) |
|---|---|
| Compound of Example 281 of U.S. Pat. No. 4,820,834 | 29.0 |
| Compound of Example 22 | 0.20 |
| Compound of Example 26 | 1.4 |
| Compound of Example 2 | 2.08 |
| Compound of Example 4 | 0.63 |
| Compound of Example 50 | 0.88 |
| Compound of Example 6 | 0.22 |

-continued

| | IC$_{50}$ (nM) |
|---|---|
| Compound of Example 8B | 55.3 |
| Compound of Example 42 | 0.44 |

Determination of selectivity for the CCK-B receptor by comparison with binding to the CCK-A receptor in rats The pancreas of an SD rat was homogenized in a 20-fold volume of 50 mM Tris-HCl buffer (pH 7.7) by the use of a Polytrone-type homogenizer, the homogenate was twice centrifuged for 10 minutes at 50000 G by the use of an ultra-centrifuge, the precipitate thus obtained was suspended in a 40-fold volume of 50 mM Tris-HCl buffer (containing 0.2% BSA, 5 mM MgCl$_2$, 0.1 mg/ml bacitracin and 5 mM DTF; pH 7.7), and the suspension was stored at –80° C. until the membrane preparations were required.

The membrane preparations were then warmed to room temperature, diluted 1:10 with the buffer and incubated at 37° C. for 30 minutes in the presence of [$^3$H]L-364,718 and the test compound then separated by suction filtration. Non-specific binding was determined in the presence of 1 μM L-364,718. The amount of labelled ligand bound to the receptor was measured by the use of a liquid scintillation counter, IC$_{50}$ values were determined, being that concentration of test compound required to inhibit specific binding by 50%.

A high affinity for the CCK-A receptor in a CCK-B/gastrin antagonist is thought to be undesirable as it may lead to side-effects such as cholestasis and gall stone formation during therapy. Therefore it is preferable for the therapeutic agent to be selective for the CCK-B receptor. This selectivity is expressed by the ratio IC$_{50}$ (CCK-A)/IC$_{50}$ (CCK-B); the higher the value of this ratio the better is the selectivity.

The table below summarises CCK-B and CCK-A binding data for examples of preferred compounds, as well as the A/B ratio. Many compounds display a marked increase in CCK-B receptor bin dine affinity when compared to the compound of Example 281 of U.S. Pat. No. 4,820,834 (also known as L-365,203). Several compounds also show greater selectivity for the CCK-B receptor over the CCK-A receptor than that reported for the compound of Example 281 of U.S. Pat. No. 4,820,834.

| | Receptor binding affinity IC$_{50}$ (nM) | | |
|---|---|---|---|
| Compound | CCK-B | CCK-A | A/B Ratio |
| Compound of Example 281 of U.S. Pat. No. 4,820,834 | 29 | 12,000 | 410 |
| Compound of Example 1 | 4.52 | 844 | 187 |
| Compound of Example 2 | 2.08 | 495 | 238 |
| Compound of Example 3 | 0.80 | 433 | 540 |
| Compound of Example 4 | 0.63 | 441 | 700 |
| Compound of Example 22 | 0.20 | 113 | 565 |
| Compound of Example 52 | 0.10 | 502 | 5020 |

Measurement of inhibition of pentagastrin-stimulated gastric acid secreation in rat A cannula was inserted into the trachea of a rat anaesthetised with urethane (intraperitoneally administered, 1.25 g/Kg), its abdominal wall was incised to expose the gastric and duodenal portions, and a polyethylene cannula was set in the anterior stomach after ligation of the cardia. The duodenum was then subjected to slight section, a polyethylene cannnula was inserted from the incised portion toward the stomach, and the pylorus was ligated to fix the cannula.

Physiological saline (with pH adjusted to 7.0) was perfused from the anterior stomach toward the pylorus at a rate of 3 ml/min, and the gastric-acid secreation was measured by continuous titration of the perfusate by the use of a pH-stat (AUT-201; product of Toa Electronics, Ltd.). The continuous titration was carried out by using 25 mM NaOH solution until the pH reached 7.0, and the result was expressed as the amount of gastric acid secreted for every 10 minutes ($\mu E_q/10$ min.). Pentagastrin was intravenously administered at a rate of 15 μg/Kg/hr.

The secretion of gastric acid increased upon administration of pentagastrin, reaching the maximum level after 60 minutes and stably maintaining this level after that. A test drug was then intravenously administered, and the secretion of gastric acid was measured; $ED_{50}$ values were determined, being the mount of the drug required to reduce the mount of secreted gastric acid down to 50% of the maximum level.

Relative $ED_{50}$ values are shown below.

|  | $ED_{50}$ (μmol/kg) |
| --- | --- |
| Compound of Example 281 of U.S. Pat. No. 4,820,834 | 4.2 |
| Compound of Example 22 | 0.011 |
| Compound of Example 42 | 0.016 |

The ruble below shows the maximum inhibition observed for representative examples. Each result is a mean for 3–5 animals.

|  | % Inhibition at 0.1 μmol/kg |
| --- | --- |
| Compound of Example 281 of U.S. Pat. No. 4,820,834 | 28 (at 0.3 μmol/kg) |
| Compound of Example 1 | 48.9 |
| Compound of Example 2 | 47.4 |
| Compound of Example 3 | 57.6 |
| Compound of Example 4 | 55.2 |
| Compound of Example 5 | 55.4 |
| Compound of Example 6 | 61.9 |

The experiments described above demonstrate that compounds of and prepared by the present invention are potent CCK-B antagonists and that they inhibit the stimulation of gastric acid release due to pentagastrin. They are therefore useful in the treatment of disease states in which the CCK-B or gastrin receptor is implicated as a mediating factor. Such disease states would include disorders of the gastrointestinal system, for example gastric and duodenal ulceration, gastritis, reflux esophagitis, Zollinger-Ellison syndrome, gastrin-sensitive pancreas, and gastrin-sensitive tumors. Disorders of the central nervous system such as anxiety and psychoses would also be amenable to treatment with the compounds of this invention. The compounds can also be used in the control of appetite and pain.

The compounds of this invention and salts thereof can be administered orally (including sublingual administration) or parenterally in the form of tablets, powders, capsules, pills, liquids, injections, suppositories, ointments and adhesive plasters.

The carrier and excipient for pharmaceutical manufacturing can be a solid or liquid, non-toxic medicinal substance, such as lactose, magnesium stearate, starch, talc, gelatin, agar, pectin, gum arabic, olive oil, sesame oil, cocoa butter, ethylene glycol and other commonly employed materials.

Examples of formulations using the compounds of this invention are described below.

Examples of tablet preparation

| Composition | 20 mg-Tablet | 40 mg-Tablet |
| --- | --- | --- |
| Compound of Example 4 | 20 mg | 40 mg |
| Lactose | 73.4 | 80 |
| Corn Starch | 18 | 20 |
| Hydroxypropylcellulose | 4 | 5 |
| Carboxymethylcellulose Ca | 4 | 4.2 |
| Mg Stearate | 0.6 | 0.8 |
| Total | 120 mg | 150 mg |

Preparation of 20 mg-tablets

Compound of Example 4 (100 g), lactose (367 g) and corn starch (90 g) were homogeneously mixed together by the use of a flow granulating coater (product of Ohgawara Seisakusho). 10% aqueous solution of hydroxypropylcellulose (200 g) was sprayed into the mixture, and granulation was then performed. After drying, the granules were filtered through a 20-mesh sieve, 20 g of carboxymethylcellulose Ca and 3 g of magnesium stearate were then added, and the mixture was treated in a rotary tablet machine equipped with a pestle of 7 mm×8.4 R (product of Ham Tekkosho), thus producing tablets each weighing 120 mg.

Preparation of 40mg-tablets

Compound of Example 4 (140 g), lactose (280 g) and corn starch (70 g) were homogeneously mixed together by the use of a flow granulating coater (product of Ohgawara Seisakusho). 10% aqueous solution of hydroxypropylcellulose (175 g) was sprayed into the mixture, and granulation was then performed. After drying, the granules were filtered through a 20-mesh sieve, 14.7 g of carboxymethylcellulose Ca and 2.8 g of magnesium stearate were then added, and the mixture was treated in a rotary tablet machine equipped with a pestle of 7.5 mm×9R (product of Hata Tekkosho), thus producing tablets each weighing 150 mg.

The clinical dosage of the compounds of this invention will be determined by the physician taking into account the precise illness, and the body weight, age, sex, medical history and other factors of the patient to be treated. In general the dosage when administered orally will be between 1 and 1000 mg/day in either a single dose or sub-divided into smaller multiple doses.

We claim:

1. A process for the production of benzodiazepines of general formula V or pharmaceutically active salts thereof which comprises the coupling reaction of an optionally substituted N-protected α-(1-benzotriazolyl)glycine derivative (II) with an aromatic or heterocyclic amino ketone (III), followed by reaction of the intermediate (IV) with ammonia and then an acid catalyzed cyclisation of the resultant amino-ketone

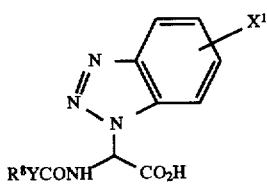

II

-continued

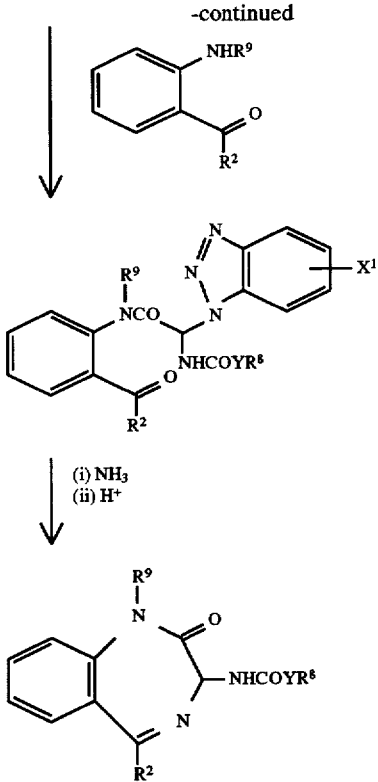

wherein:

$R^2$ is an optionally substituted aromatic carbocyclic or heterocyclic group;

$R^8$ is a linear or branched $C_1-C_6$ alkyl, a $C_3-C_8$ cycloalkyl, or an optionally substituted aralkyl, optionally substituted aryl or heteroaryl group;

$R^9$ is H, a linear or branched $C_1-C_6$ alkyl, or $CH_2COR^4$ where $R^4$ is an alkyl, a cycloalkyl, or an optionally substituted aryl, heteroaryl or saturated heterocyclic group;

$X^1$ is H, $C-C_3$ alkyl, $C_1-C_3$ alkyloxy, F, Cl or Br; and

Y is —O—, —NH— or a single bond.

2. A process according to claim 1 in which:

$R^8$ is a linear or branched $C_1-C_6$ alkyl, a $C_3-C_8$ cycloalkyl, or an optionally substituted benzyl, phenyl or heteroaryl group;

$R^9$ is H or a linear or branched $C_1-C_6$ alkyl;

$X^1$ is H; and

Y is —O—.

3. A process including the steps of claim 1 for the production of any of the following compounds or pharmaceutically acceptable salts thereof:

(a) N-((3R)-1-tert-butylcarbonylmethyl-2,3-dihydro-2-oxo-5-(2-pyridyl)-1H-1,4-benzodiazepin-3-yl)-N'-((3-dimethylamino)phenyl) urea;

(b) N-((3R)-1-tert-butylcarbonylmethyl-2,3-dihydro-2-oxo-5-(2-pyridyl)-1H-1,4-benzodiazepin-3-yl)-N'-(3-methyl (formylamino)phenyl) urea;

(c) N-((3R)-1-tert-butylcarbonylmethyl-2,3-dihydro-2-oxo-5-(2-pyridyl)-1H-1,4-benzodiazepin-3-yl)-N'-((3-methylamino)phenyl) urea;

(d) N-((3R)-1-tert-butylcarbonylmethyl-2,3-dihydro-2-oxo-5-(2-pyridyl)-1H-1,4-benzodiazepin-3-yl)-N'-(3-aminophenyl) urea;

(e) N-((3R)-1-tert-butylcarbonylmethyl-2,3-dihydro-2-oxo-5-(2-pyridyl)-1H-1,4-benzodiazepin-3-yl)-N'-(3-methylphenyl)urea; and (f) (3RS)-(ethoxycarbonyl)amino-2,3-dihydro-5-(2-pyridyl)-1H-1,4-benzodiazepin-2-one.

4. A process according to claim 1 which comprises the following reaction sequence:

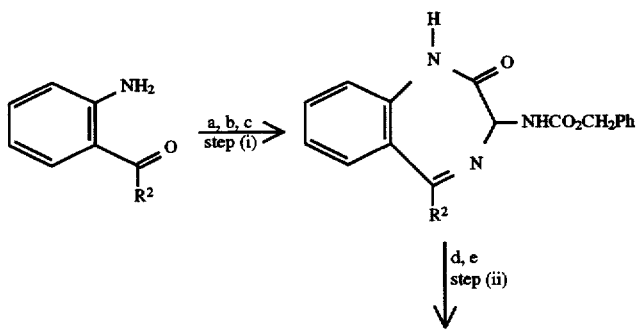

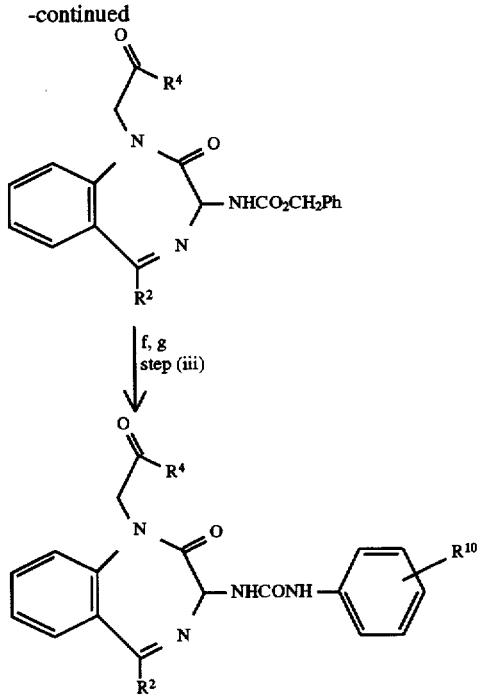

Reagents (a)

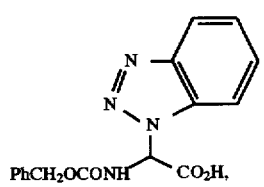

WSCI, DMP;

(b) NH₃MeOH;
(c) NH₄OAc,AcHO;
(d) NaH, DMF;
(e) R⁴COCH₂Br;
(f) HBr, DCM or H₂, Pd/C;
(g)

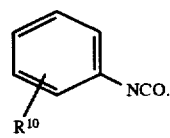

wherein:

$R^2$ is an aromatic 5- or 6-membered substituted or unsubstituted heterocycle containing at least two heteroatoms of which at least one is nitrogen, $R^4$ is an alkyl, cycloalkyl or aryl group, and $R^{10}$ is selected from the group consisting of F, Cl, Br, I, OH, CH₃, OCH₃, NO₂NHCHO, CO₂H, CN, and $NR^{11}R^{12}$, where $R^{11}$ and $R^{12}$ are independently selected from H and $C_{1-5}$ alkyl or together with the N atom they form a cyclic structure XI

(XI)

wherein a is 1–6.

5. A process according to claim 1, wherein $R^2$ is 2-pyridyl; $R^8$ is methyl, ethyl, t-butyl, or benzyl; $R^9$ is H; $X^1$ is H; and Y is —O—.

6. A process according to claim 1, wherein $R^2$ is pyridyl, pyridazinyl, pyrimidinyl, pyrazinyl, thiazolyl, isothiazolyl, methyl-imidazolyl, oxazolyl, isoxazolyl, optionally protected pyrazolyl, optionally protected imidazolyl, or optionally substituted phenyl;

$R^8$ is a linear or branched $C_1$–$C_6$ alkyl, a $C_3$–$C_8$ cycloalkyl, optionally substituted benzyl, or optionally substituted phenyl; and $R^9$ is H, a linear or branched $C_1$–$C_6$ alkyl, or CH₂COR⁴ where $R^4$ is an alkyl, a $C_3$–$C_8$ cycloalkyl, 2-methylphenyl, 3-methylphenyl, or 4-methylphenyl.

* * * * *